US012662458B2

(12) United States Patent
Hale et al.

(10) Patent No.: US 12,662,458 B2
(45) Date of Patent: Jun. 23, 2026

(54) SOLID FORMS OF A COMPOUND

(71) Applicant: Denali Therapeutics Inc., South San Francisco, CA (US)

(72) Inventors: Christopher R.H. Hale, South San Francisco, CA (US); Yingqing Ran, Foster City, CA (US); Anantha Sudhakar, Fremont, CA (US)

(73) Assignee: Denali Therapeutics Inc., South San Francisco, CA (US)

( * ) Notice: Subject to any disclaimer, the term of this patent is extended or adjusted under 35 U.S.C. 154(b) by 283 days.

(21) Appl. No.: 18/268,144

(22) PCT Filed: Dec. 17, 2021

(86) PCT No.: PCT/US2021/064069

§ 371 (c)(1),
(2) Date: Jun. 16, 2023

(87) PCT Pub. No.: WO2022/133236

PCT Pub. Date: Jun. 23, 2022

(65) Prior Publication Data

US 2024/0059662 A1 Feb. 22, 2024

Related U.S. Application Data

(60) Provisional application No. 63/127,816, filed on Dec. 18, 2020.

(51) Int. Cl.
*C07D 271/10* (2006.01)

(52) U.S. Cl.
CPC ........ *C07D 271/10* (2013.01); *C07B 2200/13* (2013.01)

(58) Field of Classification Search
CPC .................................................... C07D 271/10
See application file for complete search history.

(56) References Cited

U.S. PATENT DOCUMENTS

| | | | |
|---|---|---|---|
| 4,835,184 | A | 5/1989 | Hugelin et al. |
| 7,053,104 | B2 | 5/2006 | Van Wagenen et al. |
| 8,193,179 | B2 | 6/2012 | Hubschwerlen et al. |
| 9,408,392 | B2 | 8/2016 | O'Sullivan et al. |
| 9,421,211 | B2 | 8/2016 | Aktas et al. |
| 9,447,025 | B2 | 9/2016 | Bunker |
| 9,693,975 | B2 | 7/2017 | Bunker |
| 9,708,247 | B2 | 7/2017 | Walter et al. |
| 10,343,981 | B2 | 7/2019 | Walter et al. |
| 11,236,100 | B2 | 2/2022 | Craig, II et al. |
| 11,851,440 | B2 | 12/2023 | Craig, II et al. |
| 2001/0047100 | A1 | 11/2001 | Kjaersgaard et al. |
| 2003/0149089 | A1 | 8/2003 | Heerding et al. |
| 2008/0221100 | A1 | 9/2008 | Gless et al. |
| 2009/0131444 | A1 | 5/2009 | Reck et al. |
| 2012/0264738 | A1 | 10/2012 | Sugimoto et al. |
| 2013/0225644 | A1 | 8/2013 | Larsen et al. |
| 2013/0324551 | A1 | 12/2013 | Pulici et al. |
| 2014/0051713 | A1 | 2/2014 | Gidwani et al. |
| 2014/0121196 | A1 | 5/2014 | Sugimoto et al. |
| 2014/0275008 | A1 | 9/2014 | Xu et al. |
| 2014/0275245 | A1 | 9/2014 | Bunker |
| 2014/0378461 | A1 | 12/2014 | O'Sullivan et al. |
| 2015/0259344 | A1 | 9/2015 | Iwata et al. |
| 2016/0075654 | A1 | 3/2016 | Bunker et al. |
| 2016/0145252 | A1 | 5/2016 | Jorand-Lebrun et al. |
| 2017/0100400 | A1 | 4/2017 | Charifson et al. |
| 2017/0183355 | A1 | 6/2017 | Sprott et al. |
| 2017/0342020 | A1 | 11/2017 | Walter et al. |
| 2017/0369486 | A1 | 12/2017 | Acharya et al. |
| 2020/0331900 | A1 | 10/2020 | Craig, II et al. |
| 2021/0130308 | A1 | 5/2021 | Craig, II et al. |
| 2021/0147435 | A1 | 5/2021 | Craig, II et al. |
| 2021/0292311 | A1 | 9/2021 | Craig, II et al. |
| 2022/0106324 | A1 | 4/2022 | Sugimoto et al. |
| 2022/0177438 | A1 | 6/2022 | Craig, II et al. |
| 2022/0177456 | A1 | 6/2022 | Craig, II et al. |
| 2023/0114472 | A1 | 4/2023 | Craig, II et al. |
| 2023/0250072 | A1 | 8/2023 | Craig, II et al. |

FOREIGN PATENT DOCUMENTS

| | | |
|---|---|---|
| WO | WO-0023076 | 4/2000 |
| WO | WO-02080928 | 10/2002 |
| WO | WO-2004058730 | 7/2004 |
| WO | WO-2006028904 | 3/2006 |
| WO | WO-2006032466 | 3/2006 |
| WO | WO-2010067332 | 6/2010 |
| WO | WO-2012088365 | 6/2012 |
| WO | WO-2012121361 | 9/2012 |
| WO | WO-2012145569 | 10/2012 |
| WO | WO-2013058448 | 4/2013 |

(Continued)

OTHER PUBLICATIONS

International Search Report and Written Opinion for International Application No. PCT/US2021/064069 dated Mar. 9, 2022. 7 pages.
Alzheimer's disease [online] retrieved from the internet on Mar. 25, 2022, mayoclinic.org/diseases-conditions/alzheimers-disease/symptoms-causes/syc-. 8 pages.
Bessodes et al., Synthesis of unsaturated 4'-azido pyranosyl thymines as potential antiviral and anti-HIV agents, J. Chem. Soc. Perkin Trans. 1, 1990, pp. 3035-3039.
Chemical Abstracts Registry No. 1135218-61-9, indexed in the Registry file on STN CAS Online Apr. 16, 2009. (Year: 2009).
Chen et al., Amyloid beta: structure, biology and structure-based therapeutic development. Acta Pharmacologica Sinica 2017, pp. 1205-1235.

(Continued)

*Primary Examiner* — Shawquia Jackson
(74) *Attorney, Agent, or Firm* — Sheppard Mullin Richter & Hampton LLP

(57) ABSTRACT

Forms of 2-(4-chlorophenoxy)-N-[3-[5-[cis-3-(trifluoromethoxy)cyclobutyl]-1,3,4-oxadiazol-2-yl]-1-bicyclo[1.1.1]pentanyl]acetamide, designated herein as Compound I, were prepared and characterized in the solid state. Also provided are processes of manufacture and methods of using the forms of Compound I.

23 Claims, 12 Drawing Sheets

(56) References Cited

FOREIGN PATENT DOCUMENTS

| | | |
|---|---|---|
| WO | WO-2014144952 | 9/2014 |
| WO | WO-2014149819 | 9/2014 |
| WO | WO-2015038778 | 3/2015 |
| WO | WO-2016044331 | 3/2016 |
| WO | WO-2016059453 | 4/2016 |
| WO | WO-2016081679 | 5/2016 |
| WO | WO-2016138288 | 9/2016 |
| WO | WO-2016169911 | 10/2016 |
| WO | WO-2016177658 | 11/2016 |
| WO | WO-2017059965 | 4/2017 |
| WO | WO-2017193030 | 11/2017 |
| WO | WO-2017193034 | 11/2017 |
| WO | WO-2017193041 | 11/2017 |
| WO | WO-2017193063 | 11/2017 |
| WO | WO-2017212423 | 12/2017 |
| WO | WO-2017212425 | 12/2017 |
| WO | WO-2018009615 | 1/2018 |
| WO | WO-2018069863 | 4/2018 |
| WO | WO-2018107072 | 6/2018 |
| WO | WO-2018225093 | 12/2018 |
| WO | WO-2018227067 | 12/2018 |
| WO | WO-2019008506 | 1/2019 |
| WO | WO-2019008507 | 1/2019 |
| WO | WO-2019032743 | 2/2019 |
| WO | WO-2019046779 | 3/2019 |
| WO | WO-2019054430 | 3/2019 |
| WO | WO-2019090069 | 5/2019 |
| WO | WO-2019090074 | 5/2019 |
| WO | WO-2019090076 | 5/2019 |
| WO | WO-2019090078 | 5/2019 |
| WO | WO-2019090081 | 5/2019 |
| WO | WO-2019090082 | 5/2019 |
| WO | WO-2019090085 | 5/2019 |
| WO | WO-2019090088 | 5/2019 |
| WO | WO-2019090090 | 5/2019 |
| WO | WO-2019118785 | 6/2019 |
| WO | WO-2019183589 | 9/2019 |
| WO | WO-2019193540 | 10/2019 |
| WO | WO-2019193541 | 10/2019 |
| WO | WO-2020012339 | 1/2020 |
| WO | WO-2020031107 | 2/2020 |
| WO | WO-2020077217 | 4/2020 |
| WO | WO-2020167994 | 8/2020 |
| WO | WO-2020168011 | 8/2020 |
| WO | WO-2020181247 | 9/2020 |
| WO | WO-2020216766 | 10/2020 |
| WO | WO-2020223536 | 11/2020 |
| WO | WO-2020223538 | 11/2020 |
| WO | WO-2021151865 | 8/2021 |
| WO | WO-2022133236 | 6/2022 |
| WO | WO-2023250107 | 12/2023 |

OTHER PUBLICATIONS

Extended European Search Report for European Application No. 18850713.1 dated Mar. 30, 2021. 6 pages.

Extended European Search Report for European Application No. 18844666.0 dated Mar. 26, 2021. 10 pages.

Extended European Search Report for European Application No. 23173466.6 dated Oct. 25, 2023. 9 pages.

Hearn et al., Structure-Activity Studies of Bis-O-Arylglycolamides: Inhibitors of the Integrated Stress Response. ChemMedChem 2016, vol. 11, pp. 870-880.

International Search Report and Written Opinion for International Application No. PCT/US2018/045868 dated Nov. 26, 2018. 9 pages.

International Search Report and Written Opinion for International Application No. PCT/US2018/049197 dated Feb. 5, 2019. 12 pages.

International Search Report and Written Opinion for International Application No. PCT/US2019/023739 dated Jul. 11, 2019. 16 pages.

International Search Report and Written Opinion for International Application No. PCT/US2020/017985 dated Apr. 23, 2020. 15 pages.

International Search Report and Written Opinion for International Application No. PCT/US2020/018007 dated Apr. 21, 2020. 11 pages.

International Search Report and Written Opinion for International Application No. PCT/US2020/021534 dated May 1, 2020. 15 pages.

International Search Report and Written Opinion for International Application No. PCT/US2023/026021 dated Nov. 29, 2023. 11 pages.

Joshi et al., Small molecule modulators of eukaryotic initiation factor 2a kinases, the key regulators of protein synthesis. Biochimie 2013, vol. 95, pp. 1980-1990, XP028731042.

Kashiwagi et al., Crystal structure of eukaryotic translation initiation factor 2B. Nature 2016, vol. 531, pp. 122-125.

Kim et al., Therapeutic modulation of eIF2a phosphorylation rescues TDP-43 toxicity in amyotrophic lateral sclerosis disease models. Nature Genetics 2014, vol. 46, No. 2, pp. 152-160.

Mueller et al., PAPD5/7 Are Host Factors That Are Required for Hepatitis B Virus RNA Stabilization, Hepatology 2019, vol. 69, No. 4, pp. 1398-1411.

PubChem CID 13756165, 3,4-dihydro-2H-chromen-2-yl-(4-phenylpiperidin-1-yl)methanone, Feb. 8, 2007, 7 pages, retrieved from the internet: pubchem.ncbi.nlm.nih.gov/compound/13756165 on Sep. 17, 2020.

PubChem CID 65333682, 4-[2-(oxan-3-yl)-1,3-thiazol-4-yl]benzonitrile, Oct. 23, 2012, 8 pages, retrieved from the internet: pubchem.ncbi.nlm.nih.gov/compound/65333682 on Sep. 17, 2020.

PubChem CID 68023613, N-[5-Methoxy-6-(methoxymethyl)oxan-3-yl]heptanamide, Nov. 30, 2012, 12 pages, retrieved from the internet: pubchem.ncbi.nlm.nih.gov/compound/68023613 on Oct. 16, 2018.

PubChem CID 68310749, [(2S,5R)-5-Aminooxan-2-yl]-morpholin-4-ylmethanone, Nov. 30, 2012, 10 pages, retrieved from the internet: pubchem.ncbi.nlm.nih.gov/compound/68310749 on Sep. 17, 2020.

PubChem CID 79039022, N-[(4-hydroxyoxan-4-yl)methyl]-3-phenoxypropanamide, Oct. 19, 2014, 8 pages, retrieved from the internet: pubchem.ncbi.nlm.nih.gov/compound/79039022 on Sep. 17, 2020.

PubChem CID 828546, N-Cyclohexyl-1,2,3,4-tetrahydroisoquinoline-2-carboxamide, Jul. 9, 2005, 10 pages, retrieved from the internet: pubchem.ncbi.nlm.nih.gov/compound/828546#section=BioAssay-Results on Sep. 17, 2020.

PubChem CID 91786719, N-[(3R,4S)-4-(2-amino-2-oxoethoxy)oxan-3-yl]-4-phenoxybutanamide, Jun. 3, 2015, 9 pages, retrieved from the internet: pubchem.ncbi.nlm.nih.gov/compound/91786719 on Sep. 17, 2020.

Registry (STN) [online], Oct. 3, 2012, [retrieval date: 2022.07.25], CAS Registration No. 1398569-33-9. 1 page.

RegistryDatabaseCompounds, 2021, listing of registry database compounds. 17 pages.

RN 1449697-58-8, registry database compound, (2013). 1 page.

Sekine et al., Mutations in a translation initiation factor identify the target of a memory-enhancing compound. Science 2015, vol. 348, issue 6238, pp. 1027-1030.

Sidrauski et al., Pharmacological brake-release of mRNA translation enhances cognitive memory. eLife 2013;2:e00498 doi: 10.7554/eLife.00498. 22 pages.

Sidrauski et al., Pharmacological dimerization and activation of the exchange factor eIF2B antagonizes the integrated stress response. eLife 2015;4:e07314, doi: 10.7554/eLife.07314. 27 pages.

Surivet et al., Design, synthesis, and characterization of novel tetrahydropyran-based bacterial topoisomerase inhibitors with potent anti-gram-positive activity. Journal of Medicinal Chemistry 2013, vol. 56, No. 18, pp. 7396-7415, XP093091514.

Hilfiker et al., "Polymorphism in the Pharmaceutical Industry", Wiley-VCH, Weinheim, 2006, pp. 1-19.

Caira, Mino R., "Crystalline Polymorphism of Organic Compounds", Topics in Current Chemistry, 1998, vol. 198, pp. 163-208.

SOLID FORMS OF A COMPOUND

CROSS REFERENCE TO RELATED APPLICATIONS

This application is a U.S. National Stage Application under 35 U.S.C. § 371 of International Application No. PCT/US2021/064069, filed Dec. 17, 2021, which application claims priority to and the benefit under 35 U.S.C. § 119 (e) of U.S. Provisional Application No. 63/127,816, filed on Dec. 18, 2020, which are incorporated herein by reference in their entireties.

FIELD

The present disclosure relates generally to solid forms of compounds that modulate eukaryotic initiation factor 2B (EIF2B), pharmaceutical compositions thereof, therapeutic uses thereof, and processes for making the solid forms.

BACKGROUND

The present disclosure relates to small molecule modulators of eukaryotic initiation factor 2B (EIF2B) and their use as therapeutic agents, for example, in treating diseases such as Alzheimer's disease, Parkinson's disease, vanishing white matter disease, ALS, and frontotemporal dementia.

SUMMARY

The present disclosure provides polymorphic and/or amorphous forms of Compound I (CAS Registry number 2278265-85-1) and salts, co-crystals, solvates, and hydrates thereof. Also described herein are processes for making the forms of Compound I, pharmaceutical compositions comprising forms of Compound I, and methods for using such forms and pharmaceutical compositions in the treatment of diseases mediated by EIF2B.

DETAILED DESCRIPTION

Figure 1A:
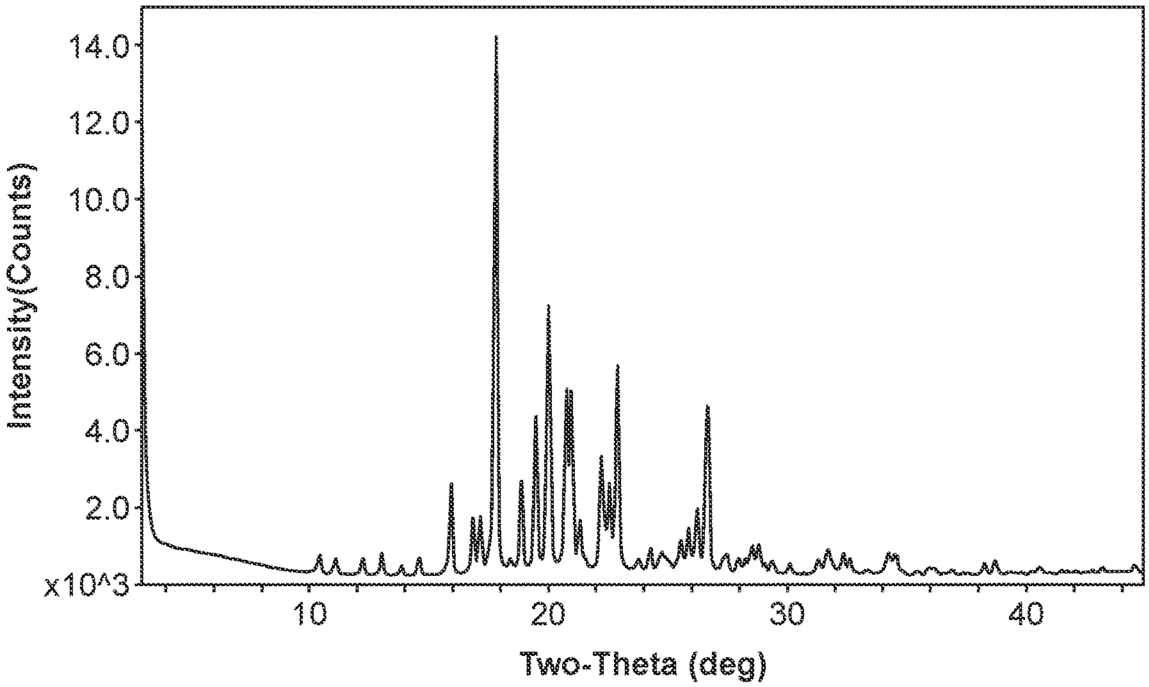
FIG. 1A is an X-ray powder diffractogram of Compound I Form A.

The compound 2-(4-chlorophenoxy)-N-[3-[5-[cis-3-(trifluoromethoxy)cyclobutyl]-1,3,4-oxadiazol-2-yl]-1-bicyclo[1.1.1]pentanyl]acetamide, designated herein as Compound I, has the following formula:

Compound I

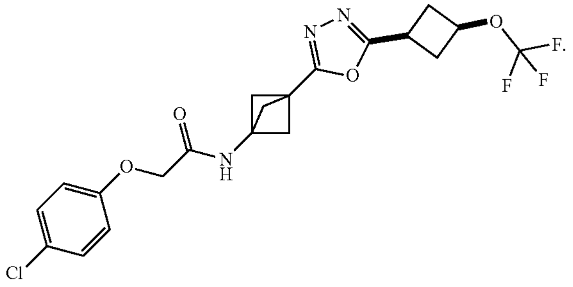

Compound I is a modulator of eukaryotic initiation factor 2B. The synthesis and method of use thereof is described in PCT International Application Publication No. WO 2019/032743 which is herein incorporated by reference in its entirety.

1. Definitions

As used in the present specification, the following words and phrases are generally intended to have the meanings as set forth below, except to the extent that the context in which they are used indicates otherwise.

The term "comprise" and variations thereof, such as, "comprises" and "comprising" are to be construed in an open, inclusive sense, that is, as "including, but not limited to." Further, the singular forms "a," "an," and "the" include plural references unless the context clearly dictates otherwise. Thus, reference to "the compound" includes a plurality of such compounds, and reference to "the assay" includes reference to one or more assays and equivalents thereof known to those skilled in the art.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±2.5%. In certain other embodiments, the term "about" includes the indicated amount±1%. Also, to the term "about X" includes description of "X".

Recitation of numeric ranges of values throughout the disclosure is intended to serve as a shorthand notation of referring individually to each separate value falling within the range inclusive of the values defining the range, and each separate value is incorporated in the specification as it were individually recited herein.

Forms of Compound I or salts, co-crystals, solvates, or hydrates thereof are provided herein. In one embodiment, reference to a form of Compound I or a salt, co-crystal, solvate, or hydrate thereof means that at least 50% to 99% (e.g., at least 50%, at least 55%, at least 60%, at least 65%, at least 70%, at least 75%, at least 80%, at least 85%, at least 90%, at least 95%, or at least 99%) of Compound I or a salt, co-crystal, solvate, or hydrate thereof present in a composition is in the designated form. For instance, in one embodiment, reference to Compound I Form A means that at least 50%, at least 55%, at least 60%, at least 65%, at least 70%, at least 75%, at least 80%, at least 85%, at least 90%, at least 95%, or at least 99% of Compound I present in a composition is Form A.

The term "solid form" refers to a type of solid-state material that includes amorphous as well as crystalline forms. The term "crystalline form" refers to polymorphs as well as solvates, hydrates, etc. The term "polymorph" refers to a particular crystal structure having particular physical properties such as X-ray diffraction, melting point, and the like.

The term "co-crystal" refers to a molecular complex of a compound disclosed herein and one or more non-ionized co-crystal formers connected via non-covalent interactions. In some embodiments, the co-crystals disclosed herein may include a non-ionized form of Compound I (e.g., Compound I free form) and one or more non-ionized co-crystal formers, where non-ionized Compound I and the co-crystal former(s) are connected through non-covalent interactions. In some embodiments, co-crystals disclosed herein may include an ionized form of Compound I (e.g., a salt of Compound I) and one or more non-ionized co-crystals formers, where ionized Compound I and the co-crystal former(s) are connected through non-covalent interactions. Co-crystals may additionally be present in anhydrous, solvated or hydrated forms. In certain instances, co-crystals may have improved properties as compared to the parent form (i.e., the free molecule, zwitterion, etc.) or a salt of the parent compound. Improved properties can be increased solubility, increased dissolution, increased bioavailability, increased dose response, decreased hygroscopicity, increased stability, a crystalline form of a normally amorphous compound, a crystalline form of a difficult to salt or unsaltable compound, decreased form diversity, more desired morphology, and the like. Methods for making and characterizing co-crystals are known to those of skill in the art.

The term "co-crystal former" or "co-former" refers to one or more pharmaceutically acceptable bases or pharmaceutically acceptable acids disclosed herein in association with Compound I, or any other compound disclosed herein.

The term "solvate" refers to a complex formed by combination of solvent molecules with molecules or ions of the solute. The solvent can be an organic compound, an inorganic compound, or a mixture of both. As used herein, the term "solvate" includes a "hydrate" (i.e., a complex formed by combination of water molecules with molecules or ions of the solute), hemi-hydrate, channel hydrate, etc. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure.

The term "desolvated" refers to a Compound I form that is a solvate as described herein, and from which solvent molecules have been partially or completely removed. Desolvation techniques to produce desolvated forms include, without limitation, exposure of a Compound I form (solvate) to a vacuum, subjecting the solvate to elevated temperature, exposing the solvate to a stream of gas, such as air or nitrogen, or any combination thereof. Thus, a desolvated Compound I form can be anhydrous, i.e., completely without solvent molecules, or partially solvated wherein solvent molecules are present in stoichiometric or non-stoichiometric amounts.

The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order (glass transition).

Any formula or structure given herein, including Compound I, is also intended to represent unlabeled forms as well as isotopically labeled forms of the compounds. It is understood that for any given atom, the isotopes may be present essentially in ratios according to their natural occurrence, or one or more particular atoms may be enhanced with respect to one or more isotopes using synthetic methods known to one skilled in the art. Thus, hydrogen includes for example $^{1}H$, $^{2}H$, $^{3}H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

As used herein, the terms "treat," "treating," "therapy," "therapies," and like terms refer to the administration of material, e.g., any one or more solid, crystalline or polymorphs of Compound I as described herein in an amount effective to prevent, alleviate, or ameliorate one or more symptoms of a disease or condition, i.e., indication, and/or to prolong the survival of the subject being treated.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

As used herein, the term "modulating" or "modulate" refers to an effect of altering a biological activity, especially a biological activity associated with a particular biomolecule such as EIF2B. For example, an agonist or antagonist of a particular biomolecule modulates the activity of that biomolecule, e.g., EIF2B, by either increasing (e.g. agonist, activator), or decreasing (e.g. antagonist, inhibitor) the activity of the biomolecule. Such activity is typically indicated in terms of an inhibitory concentration ($IC_{50}$) or excitation concentration ($EC_{50}$) of the compound for an inhibitor or activator, respectively, with respect to, for example, EIF2B.

As used herein, the term "EIF2B mediated disease or condition," refers to a disease or condition in which the biological function of EIF2B, including any mutations thereof, affects the development, course, and/or symptoms of the disease or condition, and/or in which modulation of EIF2B alters the development, course, and/or symptoms of the disease or condition. The EIF2B mediated disease or condition includes a disease or condition for which EIF2B modulation provides a therapeutic benefit, e.g. wherein treatment with compound(s), including one or more solid, crystalline or polymorphs of Compound I as described herein, provides a therapeutic benefit to the subject suffering from or at risk of the disease or condition.

As used herein, the term "composition" refers to a pharmaceutical preparation suitable for administration to an intended subject for therapeutic purposes that contains at least one pharmaceutically active compound, including any solid form thereof. The composition may include at least one pharmaceutically acceptable component to provide an improved formulation of the compound, such as a suitable carrier or excipient.

"High energy milling" refers to the mechanical reduction, in a mill, of a solid to smaller nanoparticles. Examples of high energy milling or nano-milling include wet grinding, jet milling, fluidized bed jet milling, agitated bead milling, and ball milling In some embodiments, high energy milling or nano-milling reduces the particle size to less than about 1 micron. In some embodiments the d90 for nano-milled material is less than about 900 nm, less than about 800 nm, less than about 700 nm, less than about 600 nm, less than about 500 nm, less than about 400 nm, less than about 300 nm, less than about 200 nm, or less than about 100 nm. In some embodiments the d90 for nano-milled material is less than about 100 nm. In some embodiments the d90 for nano-milled material is between 100 and 1 nm.

"D90" (or d90) means that 90% of the sample is smaller than the referenced size.

As used herein, the term "subject" or "patient" refers to a living organism that is treated with compounds as described herein, including, but not limited to, any mammal, such as a human, other primates, sports animals, animals of commercial interest such as cattle, farm animals such as horses, or pets such as dogs and cats.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated. The therapeutically effective amount will vary depending on the compound, the disorder or condition and its severity and the age, weight, etc., of the mammal to be treated. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art.

In some embodiments, the phrase "substantially shown in Figure" as applied to an X-ray powder diffractogram is meant to include a variation of ±0.2°2θ or ±0.1°2θ, as applied to DSC thermograms is meant to include a variation of ±3° Celsius, and as applied to thermogravimetric analysis (TGA) is meant to include a variation of ±2% in weight loss.

"Substantially pure form (of a polymorph)," in some embodiments, means that in the referenced material, at least 99.9% of the material is the referenced polymorph. "Substantially pure form (of a polymorph)," in some embodiments, means that in the referenced material, at least 99.5% of the material is the referenced polymorph. "Substantially pure form (of a polymorph)," in some embodiments, means that in the referenced material, at least 99% of the material is the referenced polymorph. "Substantially pure form (of a polymorph)," in some embodiments, means that in the referenced material, at least 98% of the material is the referenced polymorph. "Substantially pure form (of a polymorph)," in some embodiments, means that in the referenced material, at least 97% of the material is the referenced polymorph. "Substantially pure form (of a polymorph)," in some embodiments, means that in the referenced material, at least 96% of the material is the referenced polymorph. "Substantially pure form (of a polymorph)," in some embodiments, means that in the referenced material, at least 95% of the material is the referenced polymorph. In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

In addition, abbreviations as used herein have respective meanings as follows:

| | |
|---|---|
| CAN or MeCN | acetonitrile |
| DCM | dichloromethane |
| DMAc | dimethylacetamide |
| DMSO | dimethylsulfoxide |
| DSC | differential scanning calorimetry |
| DVS | dynamic vapor sorption |
| EtOAc | ethyl acetate |
| EtOH | ethanol |
| IPA | isopropyl alcohol |
| IPAc | isopropyl acetate |
| LC/MS | Liquid chromatography mass spectrometry |
| MeOH | methanol |
| MIBK | 4-methyl-2-pentanone |
| MTBE | methyl tert-butyl ether |
| NMR | Nuclear magnetic resonance spectroscopy |
| nPrOH | n-propanol |
| Ph | phenyl |
| RH | relative humidity |
| RT | room temperature |
| SCXRD | Single Crystal X-ray Diffraction |
| SGF | Simulated gastric fluid |
| FaSSIF | Fasting simulated small intestinal fluid |
| FeSSIF | Fed simulated small intestinal fluid |
| TGA | thermogravimetric analysis |
| THF | tetrahydrofuran |
| 2-MeTHF | 2-methyl tetrahydrofuran |
| v/v | volume to volume |
| w/w | weight to weight |
| XRPD | X-ray powder diffraction |

2. Forms of Compound I

As described generally above, the present disclosure provides crystalline forms of the compound, 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide (hereinafter "compound" of "Compound I"), and salts, co-crystals, solvates, or hydrates thereof. Crystalline forms of Compound I and salts, co-crystals, solvates, or hydrates thereof, and other forms (e.g., amorphous forms) of Compound I and salts, co-crystals, solvates, or hydrates thereof are collectively referred to herein as "forms of Compound I."

In some embodiments, Compound I is a free base. In some embodiments, Compound I is a salt or a co-crystal. In some embodiments, Compound I is a pharmaceutically acceptable salt or co-crystal. In some embodiments, Compound I is a solvate. In some embodiments, Compound I is a hydrate. In some embodiments, Compound I is an anhydrate.

In some embodiments, Compound I is an amorphous form.

Compound I Form A

In one embodiment, Compound I is crystalline and a Form A polymorph (hereinafter "Compound I Form A" or "Form A") that exhibits an X-ray powder diffraction pattern (hereinafter XRPD or diffractogram) having characteristic peaks expressed in ±0.2 degrees 2-theta at 22.2, 22.6, and 22.9.

In one embodiment, the X-ray powder diffraction pattern is made using CuKα radiation. In one embodiment, the XRPD is obtained on a diffractometer using CuKα radiation at a wavelength of about 1.54 Å.

In one embodiment, provided herein is a micronized Form A polymorph.

In one embodiment, the Form A polymorph diffractogram further comprises one or more peaks expressed in ±0.2 degrees 2-theta selected from 17.8, 20.0, 20.8, and 21.0. In one embodiment, the Form A polymorph diffractogram further comprises two or more peaks expressed in ±0.2 degrees 2-theta selected from 17.8, 20.0, 20.8, 21.0 and 26.7. In one embodiment, the Form A polymorph diffractogram further comprises three or more peaks expressed in ±0.2 degrees 2-theta selected from: 15.9, 17.8, 19.5, 20.0, 20.8, 21.0, and 26.7. In one embodiment, the Form A polymorph diffractogram further comprises one or more peaks expressed in ±0.2 degrees 2-theta selected from 15.9, 17.8, 19.5, 20.0, 20.8, 21.0, 22.2, 22.6, 22.9, and 26.7.

In one embodiment, the compound is the Form A polymorph having an X-ray powder diffraction pattern substantially free of peaks at 16.4, 16.9, 18.5, 23.3, 25.1, and 25.8±0.05 degrees 2-theta.

Figure 1B:
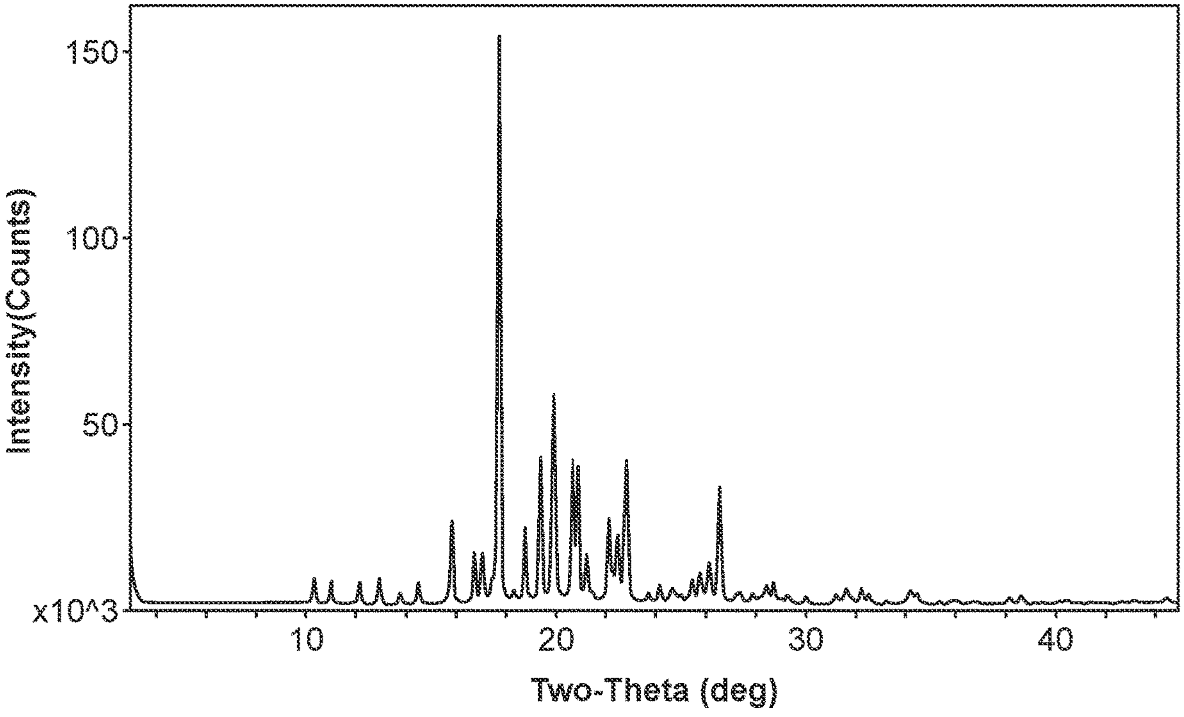
FIG. 1B is a long time X-ray powder diffractogram of Compound I Form A.

In one embodiment, Compound I Form A is characterized by the X-ray powder diffractogram substantially as shown in FIG. 1.

In one embodiment, Compound I Form A is characterized by a differential scanning calorimetry (DSC) curve that comprises an endotherm at about 126.5° C. (onset temperature). In one embodiment, Compound I Form A is characterized by the DSC curve as substantially shown in FIG. 2 (bottom line).

In one embodiment, Compound I Form A is characterized by a thermogravimetric analysis (TGA) thermogram showing a weight loss of about 0.08% up to about 150° C. In one embodiment, Compound I Form A is characterized by the thermogram as substantially shown in FIG. 2 (top line).

Figure 3:
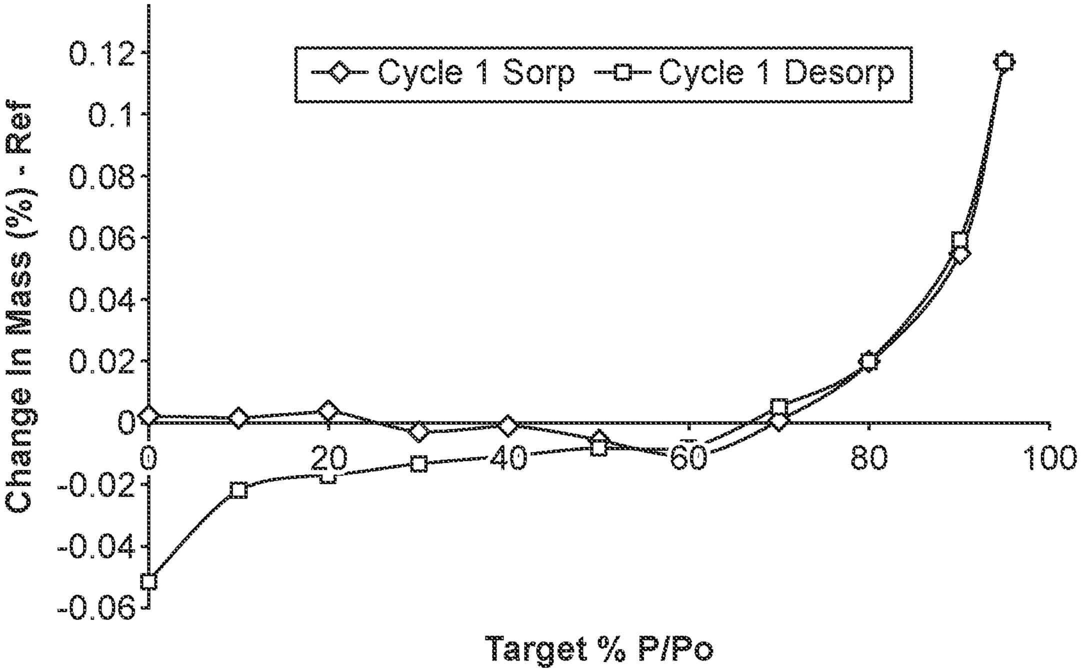
FIG. 3 is a dynamic vapor sorption (DVS isotherm plot) of Compound I Form A.

In one embodiment, Compound I Form A is characterized by a DVS Isotherm substantially as shown in FIG. 3. In one embodiment, Compound I Form A is an anhydrate. In one embodiment, Compound I Form A has an aqueous solubility of about 9.7 microgram/mL.

Some embodiments provide for Compound I Form A having unit cell parameters: a=16.8593(8) Å, b=11.0992(5) Å, c=22.4326(10) Å. Some embodiments provide for Compound I Form A having unit cell parameters: α=90°, β=96.816(2)°, γ=90°, and V=4168.0(3)$Å^3$.

In one embodiment, a single crystal of Compound I Form A is in a monoclinic crystal system and $P2_1/c$ space group. In one embodiment, Compound I Form A is characterized by one or more of the crystal structure parameters of Table 1.

In one embodiment, the Form A polymorph is a polymorph obtained by vacuum drying of a Form B polymorph described below.

In one embodiment, the Form A polymorph is produced by subjecting a solution of Compound Ito diffusion of the vapor of a counter solvent at room temperature. Amorphous compound I may be dissolved, for instance in a solvent such as dimethylacetamide, and subjected to vapor diffusion of a counter solvent, e.g., vapor of a counter solvent such as water. Other solvent counter solvent pairs include and are not limited to heptane vapor diffused into a solution of Compound I in dichloromethane, or cyclohexane vapor diffusion into a solution of Compound I in 1,4-dioxane.

Compound I Form B

In one embodiment, Compound I is crystalline and a Form B polymorph (hereinafter "Compound I Form B") that exhibits an X-ray powder diffraction pattern having characteristic peaks expressed in ±0.2 degrees 2-theta at 16.4 and 16.9.

In one embodiment, the X-ray powder diffraction pattern is made using CuKα1 radiation. In one embodiment, the XRPD is obtained on a diffractometer using CuKα1 radiation at a wavelength of about 1.54 Å.

In one embodiment, the Form B diffractogram further comprises one or more peaks expressed in ±0.2 degrees 2-theta selected from at 19.2, and 22.6. In one embodiment, the Form B diffractogram further comprises two or more peaks expressed in ±0.2 degrees 2-theta selected from at 10.2, 13.6, 19.2, and 22.6. In one embodiment, the Form B diffractogram further comprises three or more peaks expressed in ±0.2 degrees 2-theta selected from 10.2, 13.6, 19.2, 22.2, 22.6, and 27.9. In one embodiment the Form B diffractogram further comprises one or more peaks expressed in ±0.2 degrees 2-theta selected from 10.2, 13.6, 16.4, 16.9, 19.2, 22.2, 22.6, and 27.9.

In one embodiment, the compound is the Form B polymorph having an X-ray powder diffraction pattern substantially free of peaks at 18.5, 22.9, 23.3, 25.1, and 25.8, ±0.05 degrees 2-theta.

Figure 5A:
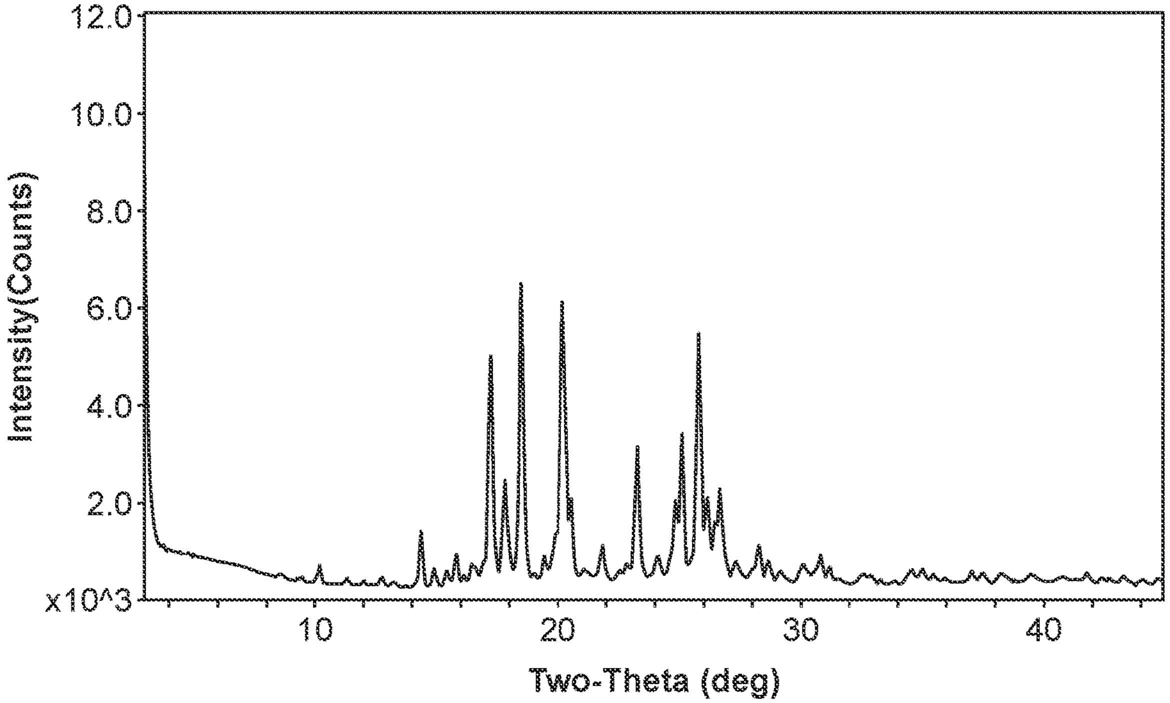
FIG. 5A is an X-ray powder diffractogram of Compound I Form C.
Figure 5B:
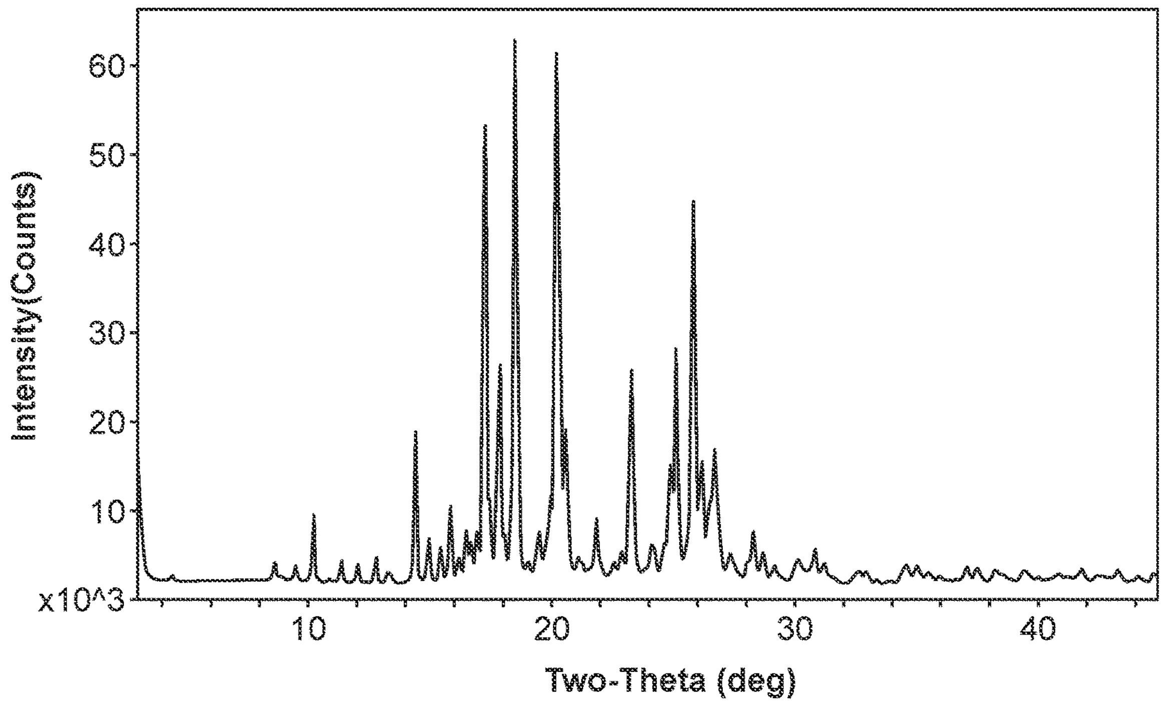
FIG. 5B is a long time X-ray powder diffractogram of Compound I Form C.

In one embodiment, the Compound I Form B is characterized by the X-ray powder diffractogram substantially as shown in FIG. 5.

In one embodiment, the Form B polymorph is a 1,4-dioxane solvate.

In one embodiment, the Form B polymorph, upon vacuum drying, converts to Form A characterized by an X-ray powder diffractogram comprising peaks expressed in ±0.2 degrees 2-theta at: 22.2, 22.6, and 22.9.

Compound I Form C

In one embodiment, crystalline Compound I is a Form C polymorph (herein after "Compound I Form C") that exhibits an X-ray powder diffraction pattern having characteristic peaks expressed in ±0.2 degrees 2-theta at 18.5, 23.3, 25.1, and 25.8.

In one embodiment, the X-ray powder diffraction pattern is made using CuKα radiation. In one embodiment, the XRPD is obtained on a diffractometer using CuKα radiation at a wavelength of about 1.54 Å.

In one embodiment, provided herein is a micronized Form C polymorph.

In one embodiment, the Form C polymorph diffractogram further comprises one or more peaks expressed in ±0.2 degrees 2-theta selected from 17.3, 17.9, and 20.2. In one embodiment, the Form C polymorph diffractogram further comprises two or more peaks expressed in ±0.2 degrees 2-theta selected from 14.4, 17.3, 17.9, 20.2, and 20.6. In one embodiment, the Form C polymorph diffractogram further comprises three or more peaks expressed in ±0.2 degrees 2-theta selected from 14.4, 17.3, 17.9, 20.2, 20.6, 26.2, and 26.7. In one embodiment, the Form C polymorph diffractogram further comprises one or more peaks expressed in ±0.2 degrees 2-theta selected from 14.4, 17.3, 17.9, 18.5, 20.2, 20.6, 23.3, 25.1, 25.8, 26.2, and 26.7.

In one embodiment, the compound is the Form C polymorph having an X-ray powder diffraction pattern substantially free of peaks at 16.4, 16.9, 22.2, 22.6, and 22.9, ±0.05 degrees 2-theta.

Figure 6:
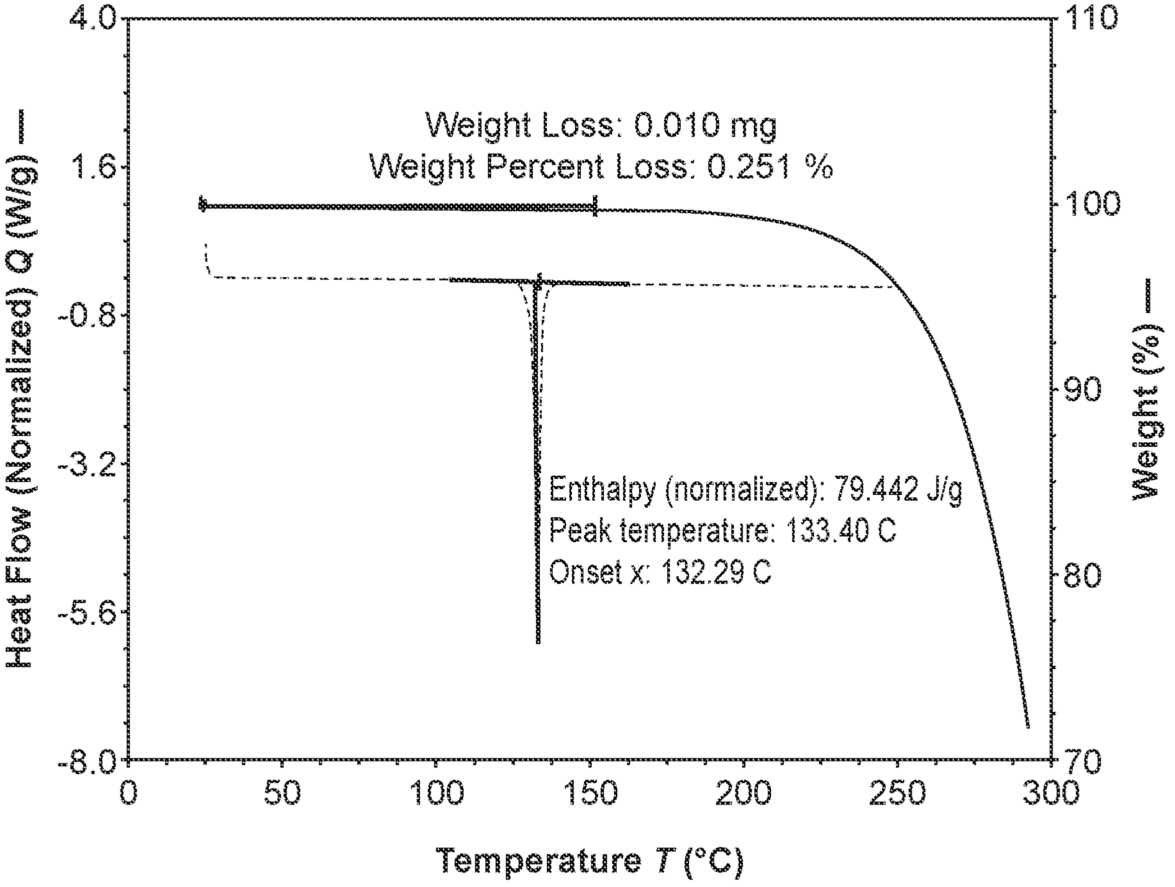
FIG. 6 is a thermogravimetric analysis (TGA) (top line) and a differential scanning calorimeter (DSC) curve (bottom line) of Compound I Form C.
Figure 7:
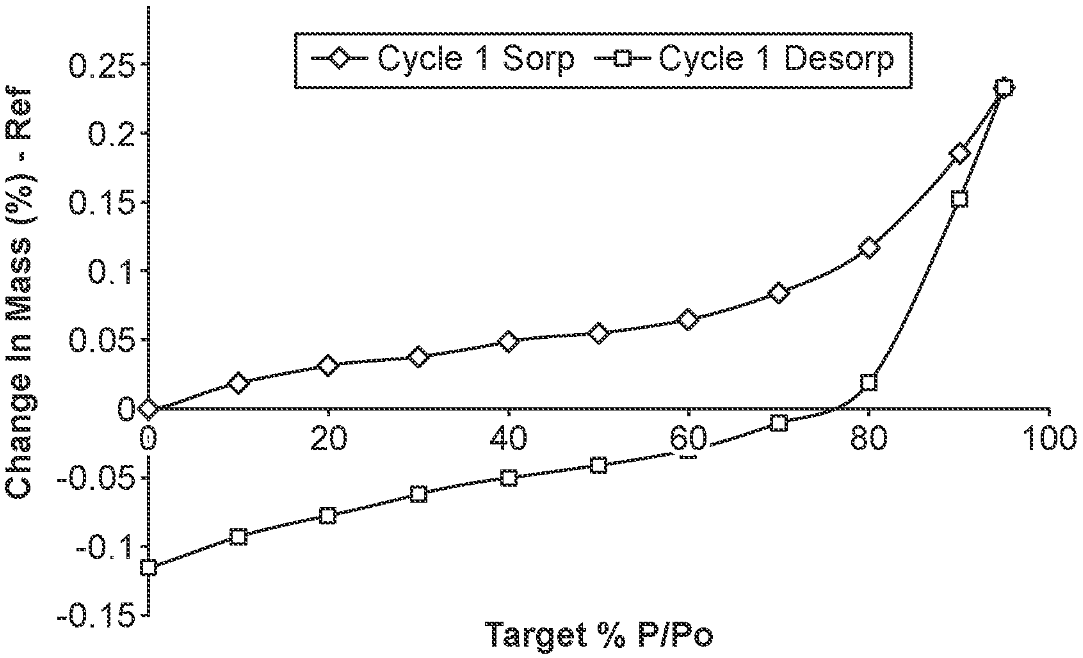
FIG. 7 is a dynamic vapor sorption (DVS isotherm plot) of Compound I Form C.
Figure 8:
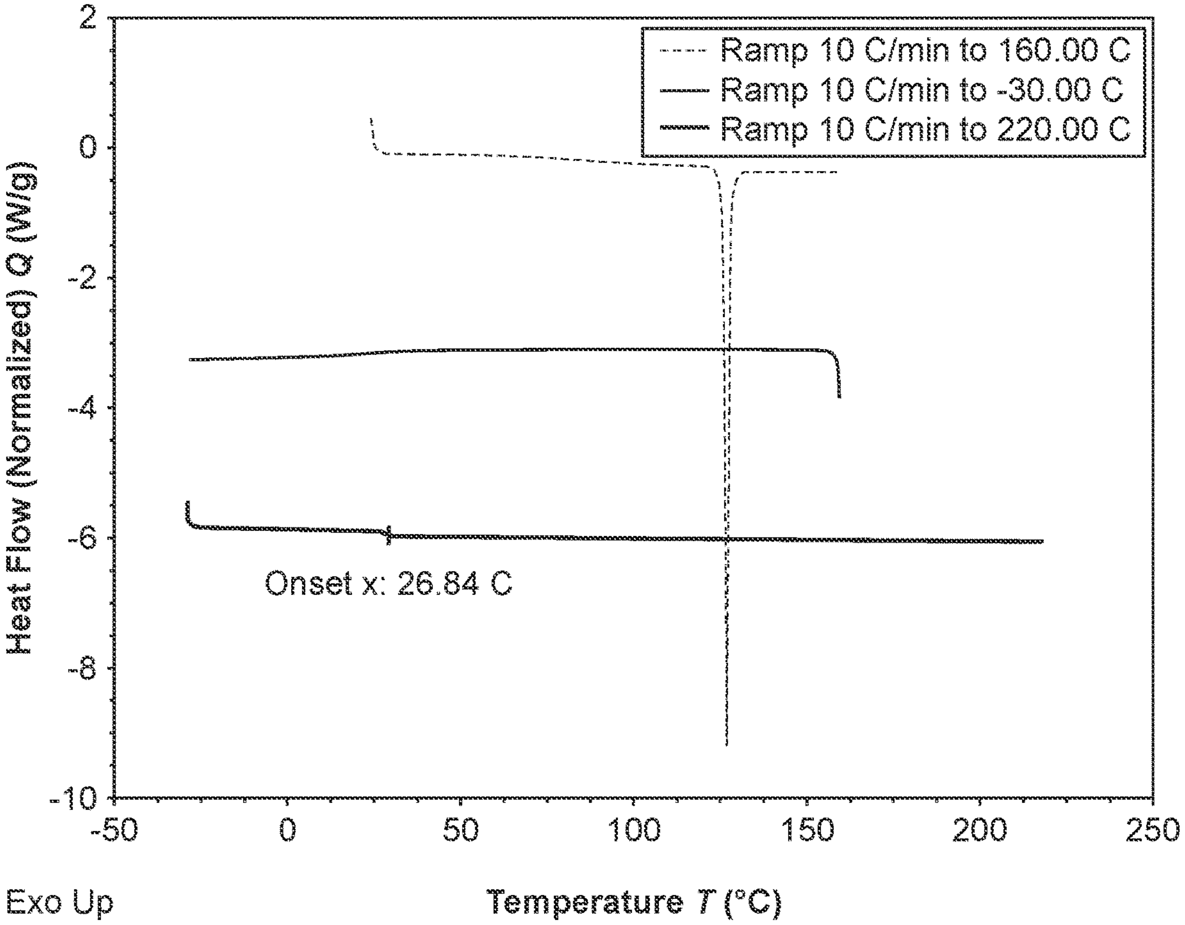
FIG. 8 is a heat-cool-heat differential scanning calorimeter (DSC) study of Compound I Form A. The bottom line represents DSC of Compound I Form D.

In one embodiment, Compound I Form C is characterized by the X-ray powder diffractogram substantially as shown in FIG. 6. In one embodiment, Compound I Form C is characterized by a differential scanning calorimetry (DSC) curve that comprises an endotherm onset at about 132.3° C. In one embodiment, Compound I Form C is characterized by a DSC curve substantially as shown in FIG. 7. In one embodiment, Compound I Form C is characterized by a DVS Isotherm substantially as shown in FIG. 8.

In one embodiment, the Compound I Form C is an anhydrate. In one embodiment, the Compound I Form C has an aqueous solubility of about 1.02 micrograms/mL.

Some embodiments provide for Compound I Form C having unit cell parameters: a=10.8945(2) Å, b=39.9519(5) Å, c=10.28331(18) Å. Some embodiments provide for Compound I Form C having unit cell parameters $\alpha$=90°, $\beta$=111.735(2)°, $\gamma$=90°, and V=4157.67(12)$Å^3$.

In one embodiment, a single crystal of Compound I Form C is in a monoclinic crystal system and $P2_1/c$ space group. In one embodiment, Compound I Form C is characterized by one or more of the crystal structure parameters of Table 2.

Unexpectedly, when Form A was subjected to high energy milling, a new polymorph was obtained. In one embodiment, Form C polymorph is produced by subjecting a Form A polymorph of 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide that exhibits an X-ray powder diffraction pattern having peaks expressed in ±0.2 degrees 2-theta at 22.2, 22.6, and 22.9, wherein the X-ray powder diffraction pattern is made using CuK$\alpha$ radiation, to high energy milling Form A was subjected to 100 polymorph screening experiments including anti-solvent addition, solid vapor diffusion, liquid vapor diffusion, slurry, evaporation, slow cooling, polymer induced crystallization, grinding, and humidity induced phase transition; none of these experiments resulted in any other stable crystals including Form C. Form C was not obtained until Form A was subjected to nano-milling, a form of high energy milling, which is not a routine method for identifying polymorphic forms. Nano-milling requires specialized equipment including a milling chamber and specialized beads (e.g., beads of suitable hardness and size for nano-milling) In some embodiments, the beads are less than or equal to 0.8 mm in diameter. In some of such embodiments, the beads are zirconia beads or yttria-stabilized zirconia beads.

In one embodiment, any crystalline compound described herein is in a substantially pure form. In one embodiment, Form C polymorph is substantially pure.

Compound I Form D

The present disclosure provides, in one embodiment, an amorphous form of 2-(4-chlorophenoxy)-N-[3-[5-[cis-3-(trifluoromethoxy)cyclobutyl]-1,3,4-oxadiazol-2-yl]-1-bicyclo[1.1.1]pentanyl]acetamide ("Compound I, Form D" or "Form D"). In one embodiment, Compound I Form D is characterized by a glass transition temperature of about 27° C. (Compound I Form D) from a heat-cool-heat differential scanning calorimetry (DSC) cycle.

In one embodiment, Compound I Form D is characterized by a differential scanning calorimetry (DSC) curve that comprises an endotherm at about 26.8° C. (onset temperature). In one embodiment, Compound I Form D is characterized by DSC substantially as shown in FIG. 8 (bottom line).

Micronization of any form of Compound I (e.g., Form A or Form C) is achieved using standard micronizing procedures, for instance, a jet mill. Particle size obtained after micronization depends on many factors such as the initial particle size, the number of passes through the micronizer, the feeder rate, the feed pressure, the mill pressure, and the like, In some embodiments, micronized Compound I (e.g., micronized Form A, micronized Form C) has a particle size distribution d90 ranging from about 1 μm to about 50 μm, 1 μm to about 40 μm, 1 μm to about 30 μm, about 1 μm to about 20 μm, about 5 μm to about 20 μm, about 5 μm to about 15 μm, or about 6 μm to about 9 μm. In some embodiments, micronized Compound I (e.g., micronized Form A, micronized Form C), has a d90<10 μm.

In some other embodiments, Compound I (e.g., Form A, Form C), is nano-milled and has a d90<1 μm. In some embodiments, Compound I (e.g., Form A, Form C), is nano-milled and has a particle size distribution d90 ranging from about 1 μm to about 1 nm. In some embodiments, Compound I (e.g., Form A, Form C), is nano-milled and has a d90<0.5 μm (500 nm). In some embodiments, Compound I (e.g., Form A, Form C), is nano-milled and has a d90<0.1 μm (100 nm). In some embodiments, Compound I (e.g., Form A, Form C), is nano-milled and has a d90<0.01 μm (10 nm).

3. Pharmaceutical Compositions, Kits, and Modes of Administration

The forms of Compound I as described herein may be administered in a pharmaceutical composition. Thus, provided herein are pharmaceutical compositions comprising one or more of the forms of Compound I described herein and one or more pharmaceutically acceptable vehicles such as carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

Some embodiments are directed to pharmaceutical compositions comprising a therapeutically effective amount of a solid form of Compound I described herein. In some embodiments, a pharmaceutical composition comprises a solid form selected from Compound I Form A, Compound I Form B, Compound I Form C, and Compound I Form D; and one or more pharmaceutically acceptable carriers.

Some embodiments are directed to pharmaceutical compositions comprising a crystalline form or amorphous form of Compound I as described herein and one or more pharmaceutically acceptable carriers. In one embodiment, a pharmaceutical composition comprises Compound I, wherein at least 95% of Compound I is in a crystalline form as described herein. In one embodiment, a pharmaceutical composition comprises Compound I, wherein at least 95% of Compound I is in an amorphous form as described herein. In one embodiment, a pharmaceutical composition comprises Compound I, wherein at least 95% of Compound I is in Form A. In one embodiment, a pharmaceutical composition comprises Compound I, wherein at least 95% of Compound I is in Form B. In one embodiment, a pharmaceutical composition comprises Compound I, wherein at least 95% of Compound I is in Form C. In one embodiment, a pharmaceutical composition comprises Compound I, wherein at least 95% of Compound I is Form D.

In one embodiment, a pharmaceutical composition comprises Compound I, wherein at least 97% of Compound I is in a crystalline form or an amorphous form as described herein. In one embodiment, a pharmaceutical composition comprises Compound I, wherein at least 97% of Compound I is in Form A. In one embodiment, a pharmaceutical composition comprises Compound I, wherein at least 97% of Compound I is in Form B. In one embodiment, a pharmaceutical composition comprises Compound I, wherein at least 97% of Compound I is in Form C. In one embodiment, a pharmaceutical composition comprises Compound I, wherein at least 97% of Compound I is in Form D.

In one embodiment, a pharmaceutical composition comprises Compound I, wherein at least 99% of Compound I is in a crystalline form as described herein. In one embodiment, a pharmaceutical composition comprises Compound I, wherein at least 99% of Compound I is in Form A. In one embodiment, a pharmaceutical composition comprises Compound I, wherein at least 99% of Compound I is in Form B. In one embodiment, a pharmaceutical composition comprises Compound I, wherein at least 99% of Compound I is in Form C. In one embodiment, a pharmaceutical composition comprises Compound I, wherein at least 99% of Compound I is in an amorphous form, i.e., Form D.

In one embodiment, a pharmaceutical composition comprises Compound I, wherein at least 99.5% of Compound I is in a crystalline form as described herein. In one embodiment, a pharmaceutical composition comprises Compound I, wherein at least 99.5% of Compound I is in Form A. In one embodiment, a pharmaceutical composition comprises Compound I, wherein at least 99.5% of Compound I is in Form B. In one embodiment, a pharmaceutical composition comprises Compound I, wherein at least 99.5% of Compound I is in Form C. In one embodiment, a pharmaceutical composition comprises Compound I, wherein at least 99.5% of Compound I is in an amorphous form, i.e., Form D.

In one embodiment, a pharmaceutical composition comprises Compound I, wherein at least 99.9% of Compound I is in a crystalline form as described herein. In one embodiment, a pharmaceutical composition comprises Compound I, wherein at least 99.9% of Compound I is in Form A. In one embodiment, a pharmaceutical composition comprises Compound I, wherein at least 99.9% of Compound I is in Form B. In one embodiment, a pharmaceutical composition comprises Compound I, wherein at least 99.9% of Compound I is in Form C. In one embodiment, a pharmaceutical composition comprises Compound I, wherein at least 99.9% of Compound I is in an amorphous form, i.e., Form D.

In some embodiments, compositions comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopherol polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, or 1 mg to 700 mg, or 5 mg to 100 mg of a compound of the present disclosure (as a free-acid, solvate (including hydrate) or salt, in any form), depending on the condition being treated, the route of administration, and the age, weight and condition of the patient. In some embodiments, unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Compound I, and any of its forms as described herein, are usually administered in the form of pharmaceutical compositions. Thus, provided herein are also pharmaceutical compositions that contain one or more of Compound I, and any of its forms as described herein, a pharmaceutically acceptable salt, stereoisomer, mixture of stereoisomers or prodrug thereof and one or more pharmaceutically acceptable vehicles selected from carriers, adjuvants and excipients. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

The pharmaceutical compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Oral administration may be another route for administration of the compounds described herein. Administration may be via, for example, capsule or enteric coated tablets. In making the pharmaceutical compositions that include at least one compound described herein or a pharmaceutically acceptable salt, isotopically enriched analog, stereoisomer, mixture of stereoisomers or prodrug thereof, the active ingredient is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, sterile injectable solutions, and sterile packaged powders. In some embodiments, oral delivery may be achieved via stick packs. Stick packs provide a compact portable unit dose form suitable for powders/granules/gels. The components of a stick pack can be sprinkled onto or mixed with food or water. In other embodiments, oral delivery may be achieved by use of sachets or pouches comprising powders/granules/gels which can be sprinkled onto or mixed with food or water.

Some examples of suitable excipients include, e.g., lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include lubricating agents such as talc, magnesium stearate and mineral oil; wetting agents; emulsifying and suspending agents; preserving agents such as methyl and propylhydroxy-benzoates; sweetening agents; and flavoring agents.

The compositions that include at least one of the forms of Compound I as described herein, can be formulated so as to provide quick, sustained or delayed release of the active ingredient after administration to the subject by employing procedures known in the art. Controlled release drug delivery systems for oral administration include osmotic pump systems and dissolutional systems containing polymer-coated reservoirs or drug-polymer matrix formulations. Another formulation for use in the methods disclosed herein employ transdermal delivery devices ("patches"). Such transdermal patches may be used to provide continuous or discontinuous infusion of the compounds described herein in controlled amounts. The construction and use of transdermal patches for the delivery of pharmaceutical agents is well known in the art. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of Compound I, and any of its forms as described herein. When referring to these preformulation compositions as homogeneous, the active ingredient may be dispersed evenly throughout the composition so that the composition may be readily subdivided into equally effective unit dosage forms such as tablets, pills and capsules.

The tablets or pills of Compound I, and any of its forms as described herein, may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described herein. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, in some embodiments orally or nasally, from devices that deliver the formulation in an appropriate manner In some embodiments, any composition described herein may further comprise a penetration enhancer.

In another aspect, the present disclosure provides kits or containers that include a Compound I, and any of its forms as described herein, or any of the pharmaceutical compositions thereof described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a bromodomain protein mediated disease or condition; the kit or container disclosed herein may include written instructions for use and/or other indication that the compound or composition is suitable or approved for administration to a mammal, e.g., a human, for a bromodomain-mediated disease or condition; and the compound or composition may be packaged in unit dose or single dose form, e.g., single dose pills, capsules, or the like.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

4. Dosing

The specific dose level of Compound I, and any of its forms as described herein, for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. In some embodiments, a dosage of from about 0.0001 to about 100 mg per kg of body weight per day, from about 0.001 to about 50 mg of compound per kg of body weight, or from about 0.01 to about 10 mg of compound per kg of body weight may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

5. Disease Indications and Modulation of EIF2B

Eukaryotic initiation factor 2B functions as a guanine nucleotide exchange factor (GEF) that catalyzes the exchange of guanosine-5'-diphosphate (GDP) with guanosine-5'-triphosphate (GTP) on eukaryotic initiation factor 2, thereby allowing the GTP bound eukaryotic initiation factor 2 to bind to the initiating methionine transfer RNA and initiate protein synthesis.

The interaction between eukaryotic initiation factor 2B and eukaryotic initiation factor 2 plays an important role in the integrated stress response (ISR) pathway. Activation of this pathway leads in part to ATF4 (Activating Transcription Factor 4) expression and stress granule formation. Aberrant ISR activation is found in multiple neurodegenerative diseases, with a strong functional link to pathology characterized by the RNA-binding/stress-granule protein TAR DNA binding protein (TARDBP), also known as TDP43. Activation of eIF2B inhibits the ISR and ISR dependent stress granule formation and is found to be neuroprotective in multiple disease models.

Impairment of eukaryotic initiation factor 2B activity is correlated to activation of the ISR pathway that is implicated in a variety of neurodegenerative diseases including Parkinson's disease, amyotrophic lateral sclerosis (ALS), Alzheimer's disease, vanishing white matter disease (VWMD), and frontotemporal dementia.

Loss-of-function mutations in EIF2B that impair protein translation can cause progressive neurodegenerative syndromes. In some neurodegenerative diseases, maladaptive PERK activation and EIF2B inhibition occur as part of the cellular response to an accumulation of misfolded proteins in the endoplasmic reticulum (Stutzbach L. D. et al., 2013, *Acta Neuropathol Commun*. July 6; 1(1):31). The resulting deficit in protein synthesis contributes to synaptic dysfunction and memory impairment. EIF2B inhibition is also linked to stress granule formation and pathogenic protein aggregation.

Restoring EIF2B activity has been shown to protect against neurodegeneration in preclinical models of prion disease, frontotemporal dementia, and ALS (Smith H. L. and Mallucci, G. R., 2016, *Brain*. 139(Pt 8):2113-21. Epub 2016 May 11).

In certain embodiments, Compound I, and any of its forms as described herein can be used to treat cellular proliferative disorders, including both cancerous and non-cancerous cellular proliferative disorders. Treatment of cellular proliferative disorders may comprise, but is not limited to, inhibiting cellular proliferation, including rapid proliferation. It is contemplated that Compound I, and any of its forms as described herein can be used to treat any type of cancer, including, but not limited to, carcinomas, sarcomas, lymphomas, leukemias and germ cell tumors. Exemplary cancers include, but are not limited to, adrenocortical carcinoma, anal cancer, appendix cancer, basal cell carcinoma, cholangiocarcinoma, bladder cancer, bone cancer, osteosarcoma or malignant fibrous histiocytoma, brain cancer (e.g., brain stem glioma, astrocytoma (e.g., cerebellar, cerebral, etc.), atypical teratoid/rhabdoid tumor, central nervous system embryonal tumors, malignant glioma, craniopharyngioma, ependymoblastoma, ependymoma, medulloblastoma, medulloepithelioma, pineal parenchymal tumors of intermediate differentiation, supratentorial primitive neuroectodermal tumors and/or pineoblastoma, visual pathway and/or hypothalamic glioma, brain and spinal cord tumors, etc.), breast cancer, bronchial tumors, carcinoid tumor (e.g., gastrointestinal, etc.), carcinoma of unknown primary, cervical cancer, chordoma, chronic myeloproliferative disorders, colon cancer, colorectal cancer, embryonal tumors, cancers of the central nervous system, endometrial cancer, ependymoma, esophageal cancer, Ewing family of tumors, eye cancer (e.g., intraocular melanoma, retinoblastoma, etc.), gallbladder cancer, gastric cancer, gastrointestinal tumor (e.g., carcinoid tumor, stromal tumor (gist), stromal cell tumor, etc.), germ cell tumor (e.g., extracranial, extragonadal, ovarian, etc.), gestational trophoblastic tumor, head and neck cancer, hepatocellular cancer, hypopharyngeal cancer, hypothalamic and visual pathway glioma, intraocular melanoma, islet cell tumors, Kaposi sarcoma, kidney cancer, large cell tumors, laryngeal cancer (e.g., acute lymphoblastic, acute myeloid, etc.), leukemia (e.g., myeloid, acute myeloid, acute lymphoblastic, chronic lymphocytic, chronic myelogenous, multiple myelogenous, hairy cell, etc.), lip and/or oral cavity cancer, liver cancer, lung cancer (e.g., non-small cell, small cell, etc.), lymphoma (e.g., AIDS-related, Burkitt, cutaneous Tcell, Hodgkin, non-Hodgkin, primary central nervous system, cutaneous T-cell, Waldenström macroglobulinemia, etc.), malignant fibrous histiocytoma of bone and/or osteosarcoma, medulloblastoma, medulloepithelioma, merkel cell carcinoma, mesothelioma, metastatic squamous neck cancer, mouth cancer, multiple endocrine neoplasia syndrome, multiple myeloma/plasma cell neoplasm, mycosis fungoides, myelodysplastic syndromes, myelodysplastic/myeloproliferative diseases (e.g., myeloproliferative disorders, chronic, etc.), nasal cavity and/or paranasal sinus cancer, nasopharyngeal cancer, neuroblastoma, oral cancer; oral cavity cancer, oropharyngeal cancer; osteosarcoma and/or malignant fibrous histiocytoma of bone; ovarian cancer (e.g., ovarian epithelial cancer, ovarian germ cell tumor, ovarian low malignant potential tumor, etc.), pancreatic cancer (e.g., islet cell tumors, etc.), papillomatosis, paranasal sinus and/or nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, prostate cancer, rectal cancer, renal cell cancer, transitional cell cancer, respiratory tract carcinoma involving the nut gene on chromosome 15, retinoblastoma, rhabdomyosarcoma, salivary gland cancer, sarcoma (e.g., Ewing family of tumors, Kaposi, soft tissue, uterine, etc.), Sézary syndrome, skin cancer (e.g., non-melanoma, melanoma, trierket cell, etc.), small intestine cancer, squamous cell carcinoma, squamous neck cancer with occult primary, metastatic, stomach cancer, supratentorial primitive neuroectodermal tumors, testicular cancer, throat cancer, thymoma and/or thymic carcinoma, thyroid cancer, transitional cell cancer of the renal, pelvis and/or ureter (e.g., trophoblastic tumor, unknown primary site carcinoma, urethral cancer, uterine cancer, endometrial, uterine sarcoma, etc.), vaginal cancer, visual pathway and/or hypothalamic glioma, vulvar cancer, Wilms tumor, and the like. Examples of noncancerous cellular proliferative disorders include, but are not limited to, fibroadenoma, adenoma, intraductal papilloma, nipple adenoma, adenosis, fibrocystic disease or changes of breast, plasma cell proliferative disorder (PCPD), restenosis, atherosclerosis, rheumatoid arthritis, myofibromatosis, fibrous hamartoma, granular lymphocyte proliferative disorders, benign hyperplasia of prostate, heavy chain diseases (HCDs), lymphoproliferative disorders, psoriasis, idiopathic pulmonary fibrosis, scleroderma, cirrhosis of the liver, IgA nephropathy, mesangial proliferative glomerulonephritis, membranoproliferative glomerulonephritis, hemangiomas, vascular and non-vascular intraocular proliferative disorders, and the like.

In certain embodiments, Compound I, and any of its forms as described herein can be used to treat lung injury and/or lung inflammation.

In certain embodiments, Compound I, and any of its forms as described herein can be used to treat cancer, pre-cancerous syndromes and diseases/injuries associated with activated unfolded protein response pathways, such as Alzheimer's disease, neuropathic pain, spinal cord injury, traumatic brain injury, ischemic stroke, stroke, Parkinson's disease, diabetes, metabolic syndrome, metabolic disorders, Huntington's disease, Creutzfeldt-Jakob Disease, fatal familial insomnia, Gerstmann-Straussler-Scheinker syndrome, and related prion diseases, amyotrophic lateral sclerosis, progressive supranuclear palsy, myocardial infarction, cardiovascular disease, inflammation, organ fibrosis, chronic and acute diseases of the liver, fatty liver disease, liver steatosis, liver fibrosis, chronic and acute diseases of the lung, lung fibrosis, chronic and acute diseases of the kidney, kidney fibrosis, chronic traumatic encephalopathy (CTE), neurodegeneration, dementias, frontotemporal dementias, tauopathies, Pick's disease, Neimann-Pick's disease, amyloidosis, cognitive impairment, atherosclerosis, ocular diseases, arrhythmias, in organ transplantation and in the transportation of organs for transplantation.

In embodiments, Compound I, and any of its forms as described herein can be used to treat or lessen the severity of cancer, Alzheimer's disease, stroke, Type 1 diabetes, Parkinson disease, Huntington's disease, amyotrophic lateral sclerosis, myocardial infarction, cardiovascular disease, atherosclerosis, arrhythmias, or age-related macular degeneration.

In certain embodiments, Compound I, and any of its forms as described herein can be used to treat neuropathic pain.

In certain embodiments, Compound I, and any of its forms as described herein can be used to treat or lessen the severity of ocular diseases/angiogenesis. In certain embodiments, the ocular disease includes vascular leakage (e.g., edema or neovascularization for any occlusive or inflammatory retinal vascular disease, such as rubeosis irides, neovascular glaucoma, pterygium, vascularized glaucoma filtering blebs, conjunctival papilloma), choroidal neovascularization (e.g., neovascular age-related macular degeneration (AMD), myopia, prior uveitis, trauma, or idiopathic), macular edema (e.g., post surgical macular edema, macular edema secondary to uveitis including retinal and/or choroidal inflammation, macular edema secondary to diabetes, and macular edema secondary to retinovascular occlusive disease (i.e. branch and central retinal vein occlusion)), retinal neovascularization due to diabetes (e.g., retinal vein occlusion, uveitis, ocular ischemic syndrome from carotid artery disease, ophthalmic or retinal artery occlusion, sickle cell retinopathy, other ischemic or occlusive neovascular retinopathies, retinopathy of prematurity, or Eale's Disease), and genetic disorders (e.g., VonHippel-Lindau syndrome). In certain embodiments, the neovascular age-related macular degeneration is wet age-related macular degeneration. In certain embodiments, the neovascular age-related macular degeneration is dry age-related macular degeneration and the patient is characterized as being at increased risk of developing wet age-related macular degeneration.

In certain embodiments, Compound I, and any of its forms as described herein can be used to treat viral infections (e.g., to prevent the initiation of viral protein synthesis). Exemplary viruses which can be treated using the compounds disclosed herein include, but are not limited to, picornaviridae (e.g., polioviruses), reoviridae (e.g., rotaviruses), togaviridae (e.g., encephalitis viruses, yellow fever virus, rubella virus, etc.), orthomyxoviridae (e.g., influenza viruses), paramyxoviridae (e.g., respiratory syncytial virus, measles virus, mumps virus, parainfluenza virus, etc.), rhabdoviridae (e.g., rabies virus), coronaviridae, bunyaviridae, flaviviridae, filoviridae, arenaviridae, bunyaviridae and retroviridae (e.g., human T-cell lymphotropic viruses (HTLV), human immunodeficiency viruses (HIV), etc.), papovaviridae (e.g., papilloma viruses), adenoviridae (e.g., adenovirus), herpesviridae (e.g., herpes simplex viruses) and poxyiridae (e.g., variola viruses). In certain embodiments, the viral infection is caused by hepatitis B virus, hepatitis C virus and/or HIV.

In certain embodiments, Compound I, and any of its forms as described herein can be used to treat disorders associated with viral infections. Such disorders include, but are not limited to neurological symptoms (e.g., encephalitis, meningoencephalitis, paralysis, myelopathy, neuropathy, aseptic meningitis, hemiparesis, dementia, dysphagia, lack of muscular coordination, impaired vision, coma, etc.), wasting symptoms (e.g., inflammatory cell infiltration, perivascular cuffing of blood vessels, demyelination, necrosis, reactive gliosis, etc.), gastroenteritis symptoms (e.g., diarrhea, vomiting, cramps, etc.), hepatitis symptoms (nausea, vomiting, right upper quadrant pain, raised liver enzyme levels (e.g., AST, ALT, etc.), jaundice, etc.), hemorrhagic fever symptoms (e.g., headache, fever, chills body pains, diarrhea, vomiting, dizziness, confusion, abnormal behavior, pharyngitis, conjunctivitis, red face, red neck, hemorrhage, organ failure, etc.), oncogenic symptoms (e.g., sarcomas, leukemias and the like, as well as "rare" malignancies, e.g., Kaposi's sarcoma, oral hairy leukoplasia, lymphomas, etc.), immunodeficiency symptoms (e.g., opportunistic infections, wasting, rare malignancies, neurological disease, fever, diarrhea, skin rashes, etc.), lesions (e.g., warts (e.g., common wart, flat wart, deep hyperkeratotic palmoplantar wart, superficial mosaic type palmoplantar wart, etc.)), epidermodysplasia, mucosal lesions, ulcers and systemic symptoms (e.g., fever, chills, headache, muscle pain, bone pain, joint pain, pharyngitis, tonsillitis, sinusitis, otitis, bronchitis, pneumonia, bronchopneumonia, nausea, vomiting, increased salivation, rash, macules, lymphadenopathy, arthritis, ulcers, photosensitivity, weight loss, irritability, restlessness, anxiety, coma, death, etc.).

In certain embodiments, Compound I, and any of its forms as described herein can be used to treat disorders characterized by unwanted synthesis and/or abnormal accumulation of one or more mutant and/or wild-type proteins. It is contemplated that the compounds disclosed herein that can inhibit translation initiation and thus can reduce the load on the protein-folding machinery and, accordingly, may reduce the severity of the disorder. Disorders associated with unwanted synthesis and/or abnormal accumulation of one or more mutant and/or wild-type proteins include, but are not limited to, Tay-Sachs disease, cystic fibrosis, phenylketonuria, Fabry disease, Alzheimer's disease, Huntington's disease, Parkinson's disease, frontotemporal dementia, congophilic angiopathy, prion related disorders (i.e., transmissible spongiform encephalopathies such as Creutzfeldt-Jacob disease, kuru, fatal familial insomnia, scrapie, bovine spongiform encephalopathy, etc.), and the like.

It is contemplated that Compound I, and any of its forms as described herein, and compositions disclosed herein, are capable of inhibiting neuronal cell death, such as in prion disease. Generally, the method includes administering a therapeutically effective amount of Compound I, and any of its forms as described herein or composition as described herein, to a patient in need of.

In some embodiments, the disorder is a neurodegenerative disease. The term "neurodegenerative disease" refers to a disease or condition in which the function of a subject's nervous system becomes impaired. Examples of neurodegenerative diseases include, e.g., Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, vanishing white matter disease, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, schizophrenia, Spinocerebellar ataxia (multiple types with varying characteristics), spinal muscular atrophy, Steele-Richardson-Olszewski disease, insulin resistance or Tabes dorsalis.

Other embodiments include use of the presently disclosed Compound I, and any of its forms as described herein in therapy. Some embodiments include their use in the treatment of a neurodegenerative disease.

In other embodiments, provided are the presently disclosed Compound I, and any of its forms as described herein for use in the treatment of Alzheimer's disease, Parkinson's disease, vanishing white matter disease, dementia, or ALS. In some embodiments, the dementia is frontotemporal dementia.

In other embodiments, provided are the presently disclosed Compound I, and any of its forms as described herein, for use enhancing cognitive memory.

In other embodiments, provided is the use of the presently disclosed Compound I, and any of its forms as described herein for the manufacture of a medicament for treating a neurodegenerative disease.

In other embodiments, provided is the use of the presently disclosed Compound I, and any of its forms as described herein for the manufacture of a medicament for treating Alzheimer's disease, Parkinson's disease, vanishing white matter disease, dementia, or ALS.

6. Biochemical Assays

Cellular stress leads to activation of the integrated stress response pathway through one of four eukaryotic initiation factor 2α kinases and halts global translation, while allowing for the translation of select transcripts like ATF4 (activating transcription factor 4) that are important for the response to cellular stress. During normal conditions, small open reading frames (ORFs) in the 5' UTR of ATF4 occupy the ribosome and prevent translation of the coding sequence of ATF4. During stress conditions however, the ribosome scans past these upstream ORFs and preferentially begins translation at the coding sequence of ATF4. In this way, the translation, and thus protein level of ATF4 is a readout of ISR pathway activation. Thus, a fusion of the uORFs and the beginning of the coding sequence of ATF to a common cellular reporter like nano-luciferase allows for a sensitive and high-throughput readout of ISR pathway activity.

Compound I, or any of its forms described herein, may be tested in the following assay. The ATF4 Nano Luciferase reporter was constructed by fusing the human full length 5' untranslated region (5'-UTR) and a small portion of the coding sequence of the ATF4 gene upstream of the Nano Luciferase (NLuc) coding sequence lacking it's start codon. Specifically, nucleotides +1 through +364 (relative to the transcriptional start site) of ATF4 transcript variant 2 (NCBI NM_182810.2) flanked 5' by EcoRI and 3' by BamHI restriction enzyme sites were synthesized and cloned into the EcoRI/BamHI cloning sites of pLVX-EF1a-IRES-Puro lentivirus vector (Clontech). Lentiviral particles were produced with Lenti-X single shots (VSV-G, Clontech) according to the manufacturer's instructions and used to transduce a human H4 neuroglioma cell line (ATCC HTB-148). H4 cells were selected with 1.25 μg/mL Puromycin, and clonal cell lines generated by limiting dilution. We utilized this cell line to generate an integrated stress response (ISR) assay to evaluate the activity of ISR pathway inhibitors via luminescence readout. The H4 ATF4-NLuc (clone 17) cell line is plated at a density of 15,000 or 2.50 cells in 96-well or 384-well respectively in DMEM+10% fetal bovine serum. 24-hours later test compounds diluted in dimethyl sulfoxide (DMSO) are added for 30 minutes at 37 degree Celsius, followed by ISR pathway activation with 50 um sodium arsenite aqueous solution for 6 additional hours. Nano Glo luciferase reagent (N1150, Promega) is added according to manufacturer instructions and the luminescence signal (corresponding to the level of ATF4 translation and thus ISR pathway activation) is read with a standard plate reader with luminescence detection capabilities. Compound I demonstrates an $IC_{50}$ of less than 1 μM in this assay.

In certain embodiments, the present disclosure provides use of Compound I, and any of its forms as described herein, or any of the pharmaceutical compositions thereof described herein in the manufacture of a medicament for the treatment of a disease or condition as described herein. In other embodiments, the present disclosure provides Compound I, and any of its forms as described herein, or any of the pharmaceutical compositions thereof described herein for use in treating a disease or condition as described herein.

EXAMPLES

Instrumental Techniques

X-ray Powder Diffraction

Standard XRPD patterns were collected using a Bruker D8 Advance diffractometer. The X-ray source is a Cu tube that was operated at 40 kV and 40 mA. The axial soller was 4.1° and the divergence slit was 0.6 mm Powder samples were prepared on zero-background Si holders using manual light pressure to keep the sample surfaces flat. Each sample was analyzed from 3 to 45°2θ with an effective step size of 0.02°2θ and 0.2 s exposure time. For a long time XRPD measurement, conditions were different: the axial soller was 2.5°; the divergence slit was 0.2 mm; the step size was 0.01°; the exposure time was 6 s.

The experimental XRPD was collected by PANalytical X'Pert$^3$ powder diffractometer using the following parameters

| Instrument | PANalytical X'Pert$^3$ |
|---|---|
| Model | Reflection mode |
| X-Ray wavelength | CuKa,<br>$Ka_1$(Å): 1.540598<br>$Ka_2$(Å): 1.544426<br>$Ka_2/Ka_1$ intensity ratio: 0.50 |
| X-Ray tube setting | 45 kV, 40 mA |
| Divergence slit | 1/8 |
| Scan mode | Continuous |
| Scan range (°2Theta) | 3°~40° |
| Scan step time (s) | 46.665 |
| Step size (°2Theta) | 0.0263 |
| Test time (h:m:s) | About 5 min |

Differential Scanning Calorimetry and Thermogravimetric Analysis

TGA characterization was conducted on a TA Instruments Discovery 55. The instrument balance was calibrated using standard weights, and the temperature calibration was performed using nickel. The nitrogen purge was 40 mL per minute at the balance and 60 mL per minute at the furnace. Each sample was placed into a pre-tared platinum pan and heated from 25° C. to 300° C. at a rate of 10° C./minute. DSC analyses were conducted on a TA Instruments Discovery 2500. Calibration of the instrument temperature and cell constant was performed using indium. The DSC cell was kept under a nitrogen purge of 60 mL per minute during each analysis. The sample was placed in a $T_{zero}$ hermetic pan with a pinhole and was heated from 25° C. to 250° C. at a rate of 10° C./minute.

Dynamic Vapor Sorption

DVS analysis was carried out using a Surface Measurement System DVS Intrinsic analyzer. The instrument was calibrated with standard weights. Approximately 15-20 mg of sample was loaded into a pan for analysis. The sample was analyzed at 25° C. in 10% relative humidity (RH) steps from 0 to 95% RH (adsorption cycle) and from 95 to 0% RH (desorption cycle). The movement from one step to the next occurred either after satisfying the equilibrium criterion of 0.002% weight change (dm/dt) or, if the equilibrium criterion was not met, after ten hours.

Example 1. Synthesis of Compound I

2-(4-chlorophenoxy)-N-[1-(hydrazinecarbonyl)-3-bicyclo[1.1.1]pentanyl]acetamide To a suspension of methyl 3-[[2-(4-chlorophenoxy)acetyl]amino]bicyclo[1.1.1]pentane-1-carboxylate (270 mg, 0.87 mmol) in EtOH (0.25-0.1M) was added hydrazine hydrate (131 mg, 2.6 mmol) in EtOH (3.5 mL) and the reaction mixture was heated at 90° C. overnight. The reaction mixture was cooled to rt often causing the product to crystallize out of solution. This solid was collected by removal of the supernatant. If the product did not crystallize, the solution was concentrated, and the crude product was sufficiently pure to use in subsequent steps.

LC-MS m/z:=310.1 $[M+H]^+$.

2-(4-chlorophenoxy)-N-[3-[5-[cis-3-(trifluoromethoxy)cyclobutyl]-1,3,4-oxadiazol-2-yl]-1-bicyclo[1.1.1]pentanyl]acetamide 2-(4-chlorophenoxy)-N-[1-(hydrazinecarbonyl)-3-bicyclo[1.1.1]pentanyl]acetamide (200 mg, 0.65 mmol), 3-cis-(trifluoromethoxy)cyclobutanecarboxylic acid (131 mg, 0.71 mmol; 8:1 to 10:1 ratio of cis- to trans-) and triethylamine ($NEt_3$) (0.45 mL, 3.23 mmol) were dissolved in EtOAc (2.6 mL) and T3P solution (0.58 mL, 1.94 mmol, 50% in EtOAc) was added. The resulting reaction mixture was heated to 100° C. overnight, cooled to rt and was diluted with sat. aq. $NaHCO_3$ solution (10 mL) and EtOAc (10 mL). The layers were separated, and the aqueous layer was extracted with EtOAc (3×10 mL). The combined organic layers were dried over anhydrous $MgSO_4$, filtered, and concentrated under reduced pressure. The crude reaction mixture was purified employing reverse-phase prep-HPLC to deliver the desired product as a clear oil. $^1$H-NMR (400 MHz; $CDCl_3$): δ7.33-7.29 (m, 2H), 7.03 (s, 1H), 6.91-6.87 (m, 2H), 4.76-4.69 (m, 1H), 4.44 (s, 2H), 3.39-3.30 (m, 1H), 2.92-2.84 (m, 2H), 2.74-2.68 (m, 2H), 2.67 (s, 6H). LC-MS m/z:=458.20 $[M+H]^+$.

Alternatively, a mixture of 2-(4-chlorophenoxy)acetic acid (50 mg, 0.27 mmol), $NEt_3$ (123 mg, 1.21 mmol) and T3P (185 mg, 0.29 mmol, 50% purity) in DCM (1 mL) was stirred at 0° C. for 1 h. To the mixture was added 1-[5-[3-cis-(trifluoromethoxy)cyclobutyl]-1,3,4-oxadiazol-2-yl]bicyclo[1.1.1]pentan-3-amine HCl salt (8:1 to 10:1 favoring the cis-diastereomer) (70 mg, 0.24 mmol) at 0° C. The mixture was stirred at 25° C. for 12 h. To the reaction was added sat. aq. $NaHCO_3$ (4 mL). The aqueous phase was extracted with DCM (5 mL, 3 mL). The combined organic phase was washed with brine (10 mL), dried with anhydrous $Na_2SO_4$, filtered and concentrated under reduced pressure to provide the title compound.

Example 2. Compound I Form A

Compound I (1.6 kg) was dissolved in isopropanol (4.8 L) at 50° C. to give a homogeneous solution. N-heptane (12 L) was added into the reaction mixture at 50° C. The solution was cooled to 15~20° C. and stirred for 30 min. The suspension was stirred for 12 hours at 20° C. The suspension was filtered, and the filter cake was washed with a premixed solution (isopropanol/n-heptane=3/7.5, v/v, 1.0 v), and n-heptane (1.6 L, 1.0 v). The filter cake was dried under vacuum at 50° C. for 12 h to give Form A (1.05 kg).

Form A can also be generated by alternative methods such as slow evaporation of a solution of Compound I in solvents including: MeOH, EtOH, IPA, IPAc, EtOAc, THF, MTBE, DCM, $CHCl_3$, toluene, 2-MeTHF, and EtOAc/acetone (1:1), and/or any combinations thereof, anti-solvent addition, solid vapor diffusion, liquid vapor diffusion, slurry, evaporation, slow cooling, polymer induced crystallization, grinding and humidity induced phase transition, or other suitable techniques.

In an alternative method, 20 mg of Form D (amorphous) was dissolved in 0.1 mL of 2-methoxyethanol. The vial containing the as-prepared clear solution was placed in a larger vial containing water (water atmosphere) to allow vapor diffusion at room temperature which produced Form A solids. Form A could also be prepared from Form D via vapor-diffusion of heptane into Form D DCM solution or cyclohexane vapor-diffusion into Form D 1,4-dioxane solution.

Form A micronization: Feeder rate=~4-5 kg/hr; Venturi pressure=120 psi; Mill pressure=60 psi. Unmicronized Compound 1 Form A (d90=420.7 um) was micronized according to the parameters listed above. Particle size distribution was measured, and the d90 was found to be 6.2 μm.

Compound I Form A was characterized by XRPD, DSC, TGA, Polarized Light Microscopy (PLM), DVS, and single-crystal X-ray diffraction. The XRPD was consistent with the theoretical XRPD calculated from the single-crystal X-ray diffraction experiment. TGA indicated low weight loss, and DSC indicated a single sharp melt at around 127° C. DVS showed that Form A is non-hygroscopic with no form change after exposure to humidity. Examination by PLM indicated irregular shaped plate-like particles.

A suitable single crystal was selected from block-like crystals and analyzed by single-crystal X-ray diffractometer.

Crystal Growth Procedure

The block-like single crystals of Form A used for SCXRD characterization were crystallized from the solvent mixture of DMAc (solvent) and $H_2O$ (anti-solvent) by liquid vapor diffusion.

Data Collection

A suitable single crystal with good diffraction quality was selected out from the block-like crystal sample and wrapped with Paratone-N (an oil based cryoprotectant). The crystal was mounted on a mylar loop in a random orientation and immersed in a stream of nitrogen at 119.99 K. Preliminary examination and data collection were performed on a Bruker D8 Venture (CuKα radiation, λ=1.54178 Å) diffractometer and analyzed with the APEX3 software package. Cell parameters and an orientation matrix for data collection were retrieved and refined (least-squares refinement) by SAINT (Bruker, V8.37A, after 2013) software using the setting angles of 9708 reflections in the range 3.983°<θ<66.686°. The data were collected to a minimum diffraction angle (θ) of 2.639° and a maximum diffraction angle (θ) of 66.760°. The data set was 99.0% complete, having a Mean I/σ of 33.6 and D min (Cu) of 0.84 θ.

Data Reduction

Frames were integrated with SAINT (Bruker, V8.37A, after 2013). A total of 58799 reflections were collected, of which 7337 were unique. A multi-scan absorption correction was performed using SADABS-2014/5 (Bruker, 2014/5). The absorption coefficient μ of this material is 2.165 $mm^{-1}$ at this wavelength (λ=1.54178 Å) and the minimum and maximum transmissions are 0.6197 and 0.7528. The $R_{int}$ value was 4.54% based on intensity.

Single Crystal Structure Solution and Refinement

The structure was solved in the space group $P2_1/c$ with the ShelXT structure solution program using Intrinsic Phasing and refined with ShelXL (Version 2017/1) refinement package using full-matrix least-squares on $F^2$ contained in OLEX2. All non-hydrogen atoms were refined anisotropically. The positions of all hydrogen atoms were calculated geometrically and refined using the riding model.

Calculated X-ray Powder Diffraction (XRPD) Pattern

The calculated XRPD pattern was generated for Cu radiation using Mercury program and the atomic coordinates, space group, and unit cell parameters from the single crystal structure.

Single Crystal Structure Diagrams

The crystal structure representations were generated by OlEX2 and Diamond. The thermal ellipsoids drawing was generated by ORTEP-III.

Theoretical XRPD Pattern

The theoretical XRPD pattern was generated for Cu radiation using Mercury program and the atomic coordinates, space group, and unit cell parameters from the single crystal structure.

TABLE 1

Structural information and refinement parameters for Compound I Form A single crystal

| | |
|---|---|
| Empirical formula | $C_{20}H_{19}ClF_3N_3O_4$ |
| Formula weight | 457.83 |
| Temperature | 119.99 K |
| Wavelength | CuKa (λ = 1.54178 Å) |
| Crystal system, space group | monoclinic, $P2_1/c$ |
| Unit cell dimensions | a = 16.8593(8) |
| | b = 11.0992(5) |
| | c = 22.4326(10) |
| | α = 90° |
| | β = 96.816(2)° |
| | γ = 90° |
| Volume | 4168.0(3) $Å^3$ |
| Z, Calculated density | 8, 1.459 $g/cm^3$ |
| Absorption coefficient | 2.165 $mm^{-1}$ |
| F(000) | 1888.0 |
| Crystal size | 0.2 × 0.2 × 0.2 $mm^3$ |
| 2 Theta range for data collection | 5.278 to 133.52 |
| Limiting indices | −19 ≤ h ≤ 17 |
| | −13 ≤ k ≤ 13 |
| | −26 ≤ l ≤ 26 |
| Reflections collected/Independent reflections | 58799/7337 [$R_{int}$ = 0.0454, $R_{sigma}$ = 0.0298] |
| Refinement method | Full-matrix least-squares on $F^2$ |
| Data/restraints/parameters | 7337/0/559 |
| Goodness-of-fit on $F^2$ | 1.034 |
| Final R indices [I ≥ 2sigma(I)] | $R_1$ = 0.0438, $wR_2$ = 0.1157 |
| Final R indices [all data] | $R_1$ = 0.0463, $wR_2$ = 0.1177 |
| Largest diff. peak and hole | 0.72/−0.35 e · $Å^{-3}$ |

The SCXRD characterization and structural analysis suggested that the crystal system of the single crystal is monoclinic and the space group is $P2_1/c$, the cell parameters are:

a=16.8593(8) Å, b=11.0992(5) Å, c=22.4326(10) Å, α=90°, β=96.816(2)°, γ=90°, V=4168.0(3)$Å^3$. The formula weight is 457.83 $g \cdot mol^{-1}$ with Z=8, resulting in the calculated density of 1.459 $g \cdot cm^3$. The calculated XRPD pattern of Compound I Form A from single crystal was in agreement with the experimental XRPD pattern.

Example 3. Compound I Form B

A 1,4-dioxane solution of Form A was prepared by dissolving 20 mg in 0.2-1.0 mL of 1,4-dioxane until clear solution was obtained. Then, water was added while maintaining magnetic agitation until precipitate appeared. Form B converted to Form A after vacuum drying at room temperature. XRPD data was obtained on the wet-cake prior to drying.

Figure 4:
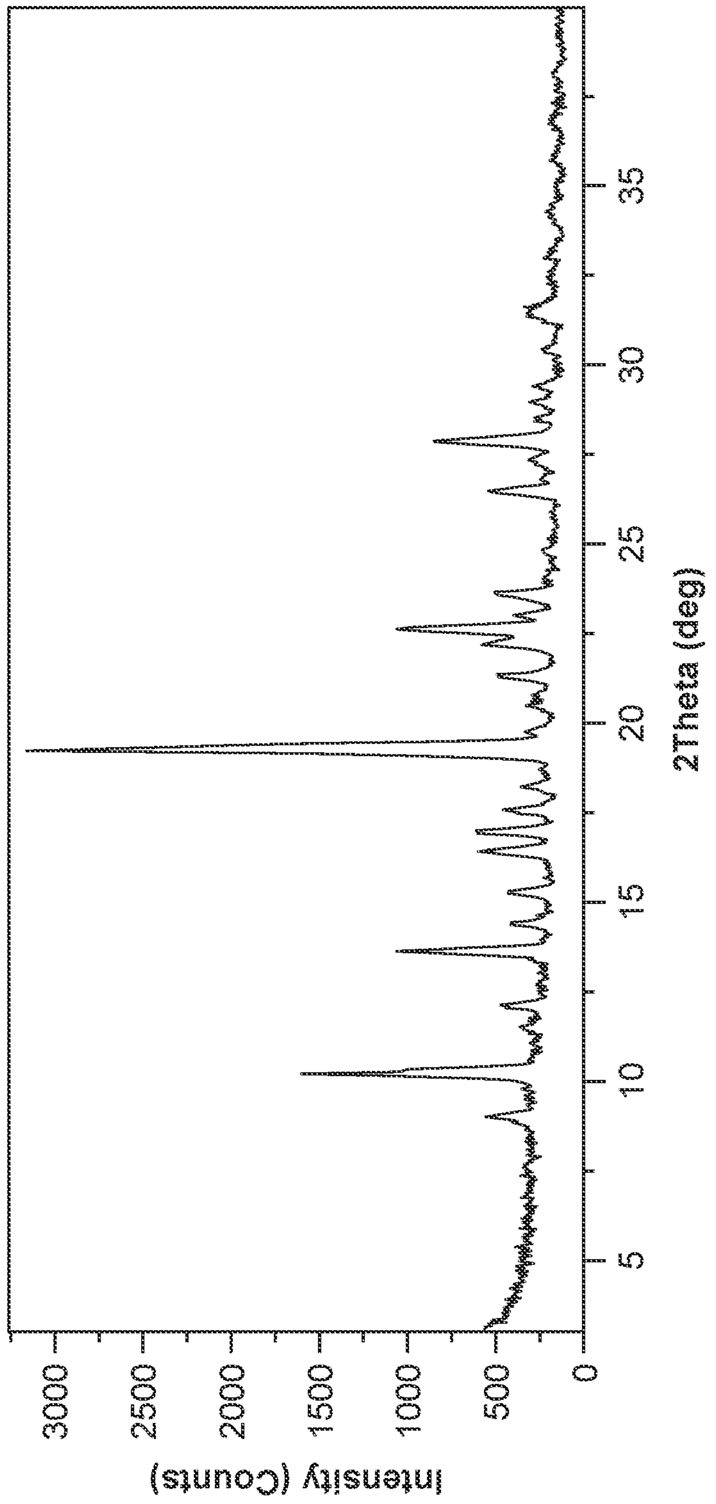
FIG. 4 is an X-ray powder diffractogram of Compound I Form B.

Due to the instability of Form B, it was only characterized by XRPD. Based on the method of preparation, it is believed to be a 1,4-dioxane solvate. FIG. 4 is an X-ray powder diffractogram of Compound I Form B.

Example 4. Compound I Form C 200 g of 0.8 mm zirconia beads (grinding media) were charged into the grinding cylinder of a DynoMill RL. Then, approximately 50 g of Form A material was suspended in 400 mL of vehicle (0.5%. HPMC E5, 0.5% PVP K30, 0.2% SLS in water) and added into the feeding hopper. The suspensions were then ground at 3000 rpm for ~3 hours and at 2000 rpm for ~2 hours until the PSD target of d90<500 nm was achieved (nano-milling) The suspension was then discharged from the mill, and the mill was rinsed and recirculated with 50 mL of vehicle two times. The wet-nanosuspension was then mixed with mannitol (1:1 mannitol:Form A mass ratio) and sprayed-dried using a ProCepT 4M8Trix according to the parameters below. The spray-dried powder was then dried under vacuum at 30° C. for overnight.

| Parameters | Setting |
|---|---|
| Instrument | Procept (4M8-Trix) |
| API conc. (mg/mL) | ~100 |
| Nozzle orifice size (mm) | 1 |
| Inlet Gas Flow ($m^3$/min) | 0.40 |
| Set inlet Temp. (° C.) | 110 |
| Column out Temp. (° C.) | 51.3 |
| Cyclone in Temp. (° C.) | 46.4 |
| Cyclone Gas pressure (bar) | 0.14 |
| Set Nozzle Gas pressure (bar) | 1.33 |
| Cyclone size | Medium |
| Pump speed (rpm) | 85 |
| Liquid flow (g/min) | 3.5 |
| Yield (%) | ~80 |

2 g of the above-produced spray-dried nanosuspension (SDN) was then suspended in 5 mL of water and stirred at 25° C. for about 18 hours. The solids were then isolated by centrifugation and rinsed with water 5 times, dried under vacuum at 40° C., and characterized by DSC and XRPD which revealed Form C.

Subsequent to obtaining Form C by nano-milling of Form A, as described above, Form C could also be obtained by other methods in locations where Form C had been previously formed or in locations previously exposed to Form C. In such an environment, Form C was also observed to form under a variety of conditions including by slow evaporation of solutions of Compound I in MeOH, EtOH, nPrOH, IPA, acetone, MIBK, EtOAc, IPAc, ethyl formate, butyl formate, 1,4-dioxane, diethylether, MTBE, 2-methoxyethanol, dimethoxyethane, acetonitrile, toluene, DCM, chloroform, and THF, and/or any combinations thereof, anti-solvent addition, solid vapor diffusion, liquid vapor diffusion, slurry, evaporation, slow cooling, polymer induced crystallization, grinding and humidity induced phase transition, or other suitable techniques.

Micronization of Form C: Where Form C was obtained by other such methods including seeding, Form C was optionally micronized using the following parameters: Feeder rate=~1.5 kg/hr; Feed pressure=6.0 bar; Mill pressure=5.5 bar. Unmicronized Compound I Form C (d90=90 μm) was micronized according to these parameters listed for a total of 4 passes to achieve a d90 of 9 μm. The d90 after the 1st, 2nd, and 3rd passes were 19, 13, and 10 μm, respectively. Micronization methods are known and include but are not limited to jet milling, high shear wet milling, and ball milling Form C was characterized by XRPD, single-crystal X-ray diffraction, TGA, DSC, PLM, and DVS. XRPD revealed a crystalline structure, and the calculated XRPD pattern was consistent with the experimental data. TGA indicated low-weight loss, and the DSC showed a single sharp melt at about 133° C. DVS study showed there was no weight change and no polymorphic change after exposure to humidity. PLM showed rod-like particle morphology. The data are consistent with Form C existing as an anhydrate form.

Crystal Growth Procedure

During preparation of saturated Form A IPA/water solution, Form C crystals with high crystallinity were obtained after cooling the solution. The melting point of crystals prepared by cooling IPA/water solution is about 133.8° C. The crystals obtained by this method are Form C with high crystallinity. One crystal having a size of 0.1×0.08×0.05 mm was used for SCXRD.

Single-Crystal X-Ray Diffractometry (SCXRD)

SCXRD were collected using a Rigaku SuperNova diffractometer. The X-ray source is a Cu tube, operated at 50 kV and 0.8 mA. A suitable single crystal was selected and mounted on a glass fiber. The crystal was kept at a steady temperature at 223 K during data collection. Data were measured using ω scans of 1.0° per frame for 2.0/8.0 s. Preliminary examination and data collection were performed and analyzed with the CrysAlisPro software package. Cell parameters and an orientation matrix for data collection were retrieved and refined (least-squares refinement) by CrysAlisPro software using the setting angles of 8555 reflections in the range 4.3550°<θ<75.9450°. The data were collected to a minimum diffraction angle (θ) of 4.37° and a maximum diffraction angle (θ) of 76.05°. The final data completeness was 97.50%, having a Mean I/σ of 20.3 and D min (Cu) of 0.79 Å.

Data Reduction

Frames were integrated with CrysAlisPro (Rigaku OD, 2018). A total of 17775 reflections were collected, of which 8457 were unique. A multi-scan absorption correction was performed using spherical harmonics as implemented in SCALE3 ABSPACK. The absorption coefficient μ of this material is 2.170 $mm^{-1}$ and the minimum and maximum transmissions are 0.82248 and 1.00000. The $R_{int}$ value was 3.95% based on intensity.

Single Crystal Structure Solution and Refinement

The structure was solved in the space group $P2_{1/c}$ with the XS (Sheldrick, 2008) structure solution program using the direct solution method and by using Olex2 (Dolomanov et al., 2009) as the graphical interface. The model was refined with version of XH (Sheldrick, 2008) using full matrix least squares on F2 minimization. All non-hydrogen atoms were refined anisotropically. The positions of all hydrogen atoms were calculated geometrically and refined using the riding model.

Single Crystal Structure Diagrams

The crystal structure representations and the thermal ellipsoids drawings were generated by Diamond.

Theoretical XRPD Pattern

The theoretical XRPD pattern was generated for Cu radiation using Mercury program and the atomic coordinates, space group, and unit cell parameters from the single crystal structure.

TABLE 2

Structural information and refinement parameters for Compound I Form C single crystal

| | |
|---|---|
| Empirical formula | $C_{20}H_{19}ClF_3N_3O_4$ |
| Formula weight | 457.83 |
| Temperature | 223.00 K |
| Wavelength | CuKa (λ = 1.54184 Å) |
| Crystal system, space group | Monoclinic, P21/c |
| Unit cell dimensions | a = 10.8945(2) Å<br>b = 39.9519(5) Å<br>c = 10.28331(18) Å<br>α = 90°<br>β = 111.735(2)°<br>γ = 90° |
| Volume | 3 4157.67(12) Å |
| Z, Calculated density | 8, 1.463 g/cm$^3$ |
| Absorption coefficient | 2.170 mm$^{-1}$ |
| F(000) | 1888 |
| Crystal size | 0.10 × 0.08 × 0.05 mm$^3$ |
| 2 Theta range for data collection | 8.74 to 152.10 |
| Limiting indices | −9 ≤ h ≤ 13<br>−49 ≤ k ≤ 42<br>−12 ≤ l ≤ 12 |
| Reflections collected/Independent reflections | 17775/8457 [$R_{int}$ = 0.0395] |
| Refinement method | Full-matrix least-squares on $F^2$ |
| Data/restraints/parameters | 6940/0/597 |
| Goodness-of-fit on F2 | 1.031 |
| Final R indices [I ≥ 2sigma(I)] | $R_1$ = 0.0572, $wR_2$ = 0.1540 |
| Final R indices [all data] | $R_1$ = 0.0689, $wR_2$ = 0.1661 |
| Largest diff. peak and hole | 0.979/−0.411 e · Å$^{-3}$ |

The structure of the single crystal of Form C was determined successfully. The crystal system of the single crystal is monoclinic and the space group is P21/ c, the cell parameters are: a=10.8945(2) Å, b=39.9519(5) Å, c=10.28331(18) Å, α=90°, β=111.735(2)°, γ=90°, V=4157.67(12)Å3. The formula weight is 457.83 g·mol-1 with Z=8. The molecules observed in the asymmetric unit is consistent with the Formula I chemical structure and there are two Formula I molecules in the asymmetric unit. The theoretical XRPD calculated from single crystal structure was in agreement with the experimental XRPD of Form C.

It should be noted that in the standard condition XRPD, diffraction peaks below 10°2θ are not obvious but they can be clearly observed in the long time XRPD measurement. The observed low angle diffraction peaks are validated by the theoretical XRPD.

Example 5. Compound I Form D

Form A was kept in an oven at 150° C. until all solids melted. The melt was kept at 150° C. for 5 minutes and was then taken out of the oven and cooled to room temperature. Form D was stable for 7 days when stored at 5° C. but converted to Form C at RT-60° C.

Figure 9:
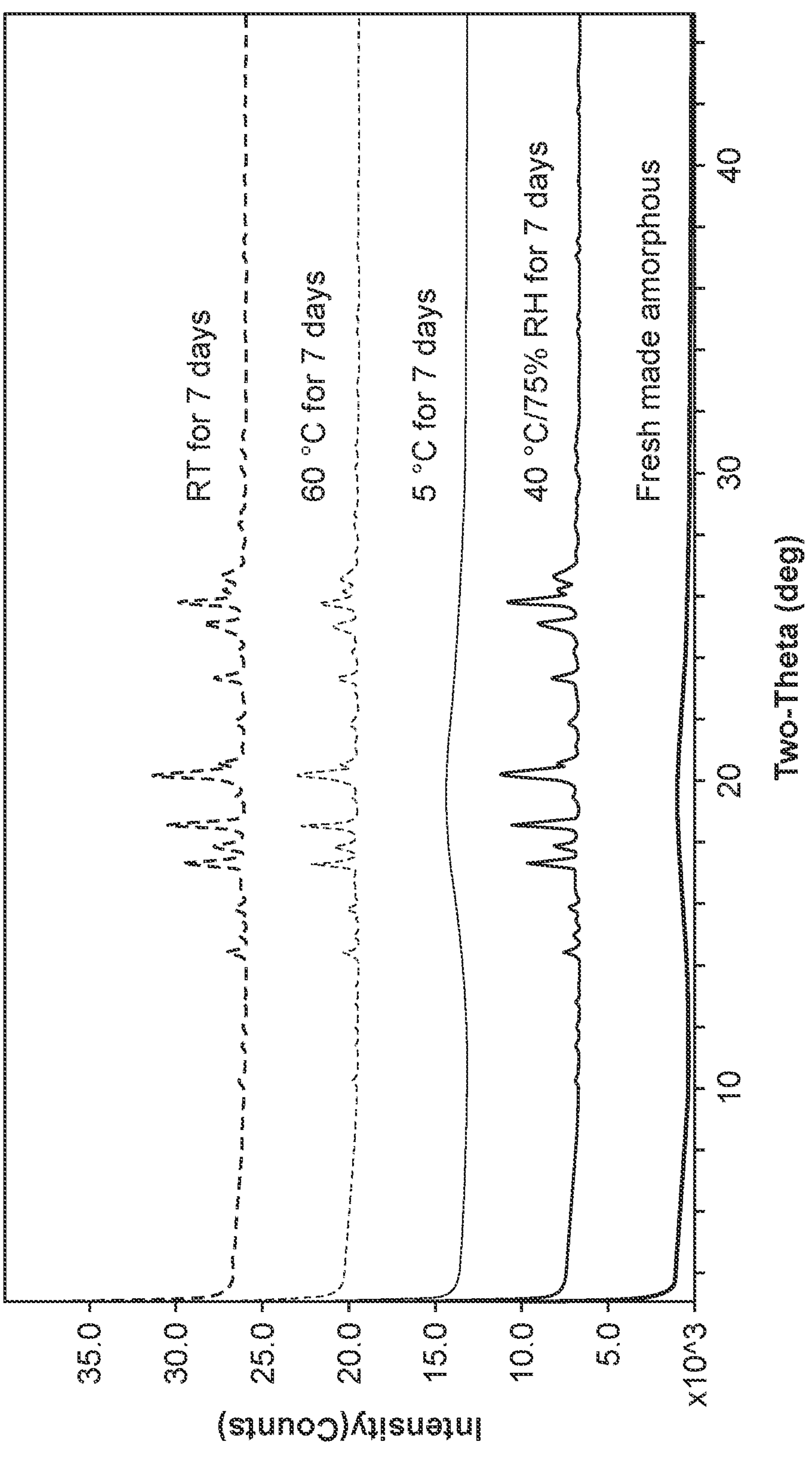
FIG. 9 shows X-ray powder diffractograms of Compound I Form D, freshly made (bottom), and upon storage for 7 days under different conditions.
Figure 10A:
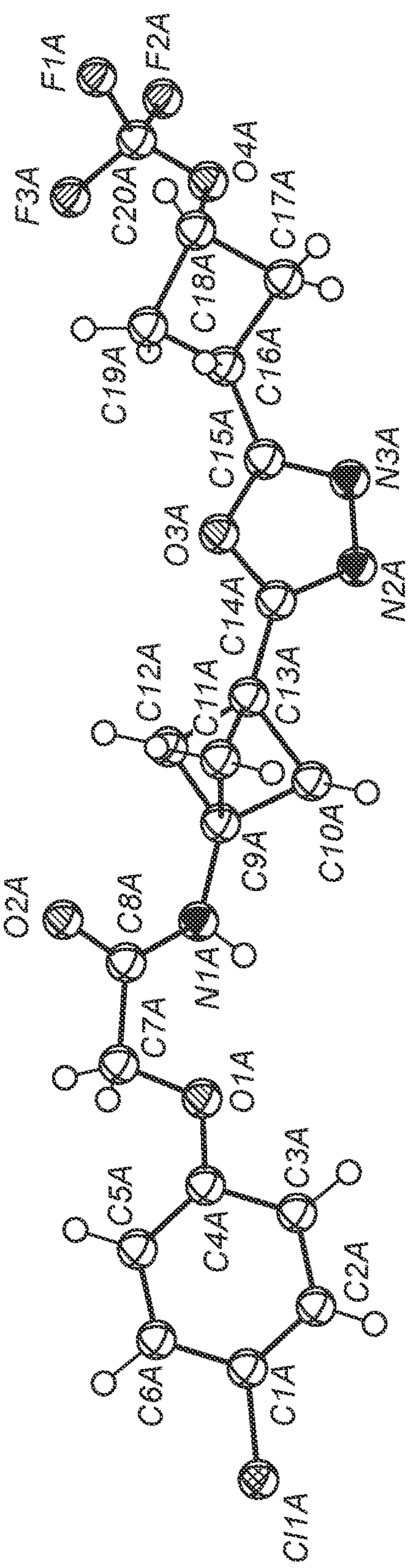
FIG. 10A depicts a thermal ellipsoid (ORTEP) drawing of Compound I Form A, asymmetric unit molecule 1.
Figure 10B:
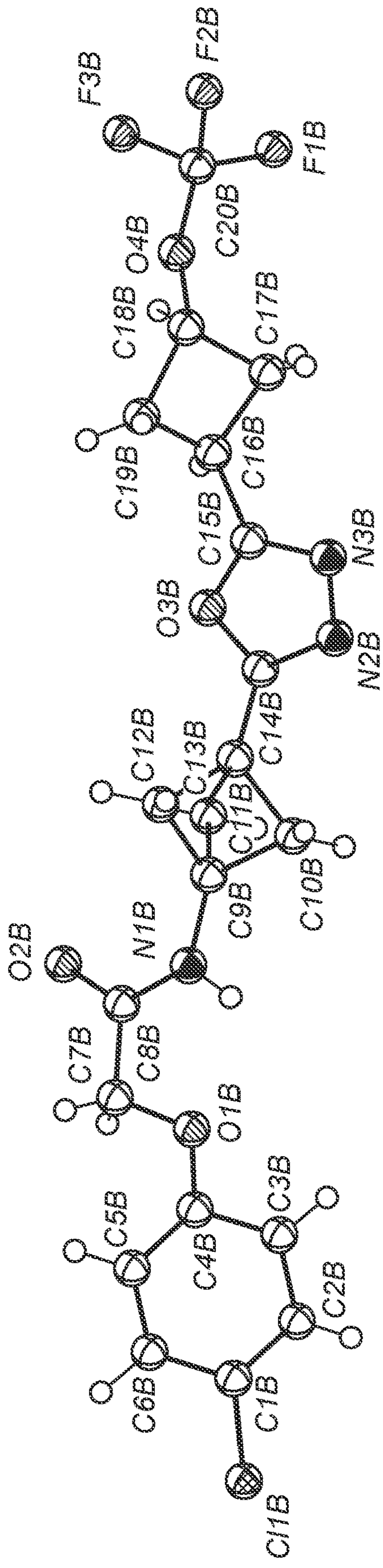
FIG. 10B depicts a thermal ellipsoid (ORTEP) drawing of Compound I Form A, asymmetric unit molecule 2.
Figure 11A:
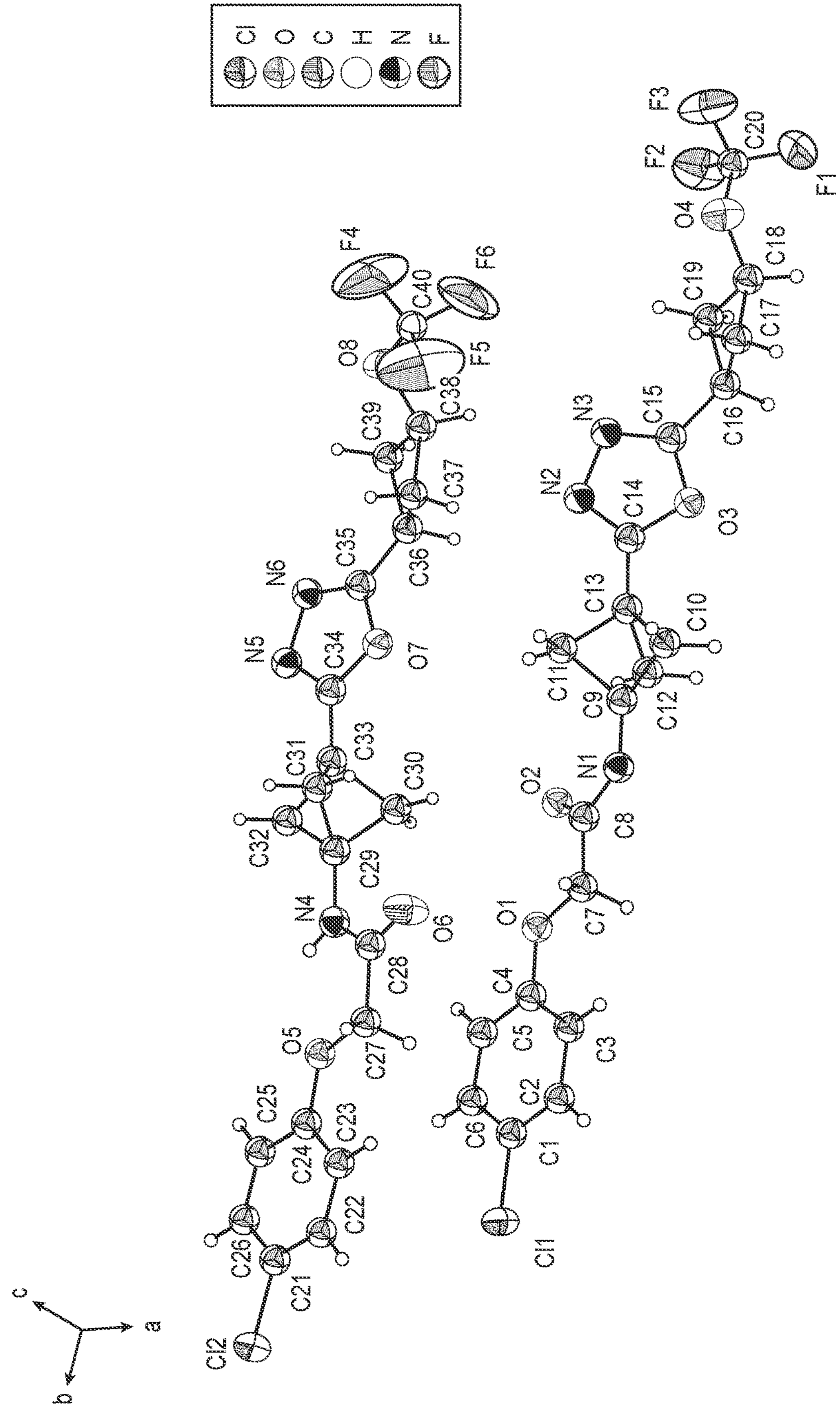
FIG. 11A shows thermal ellipsoid drawing of Compound I Form C asymmetric unit (Part 1 of the disorder in $—OCF_3$).
Figure 11B:
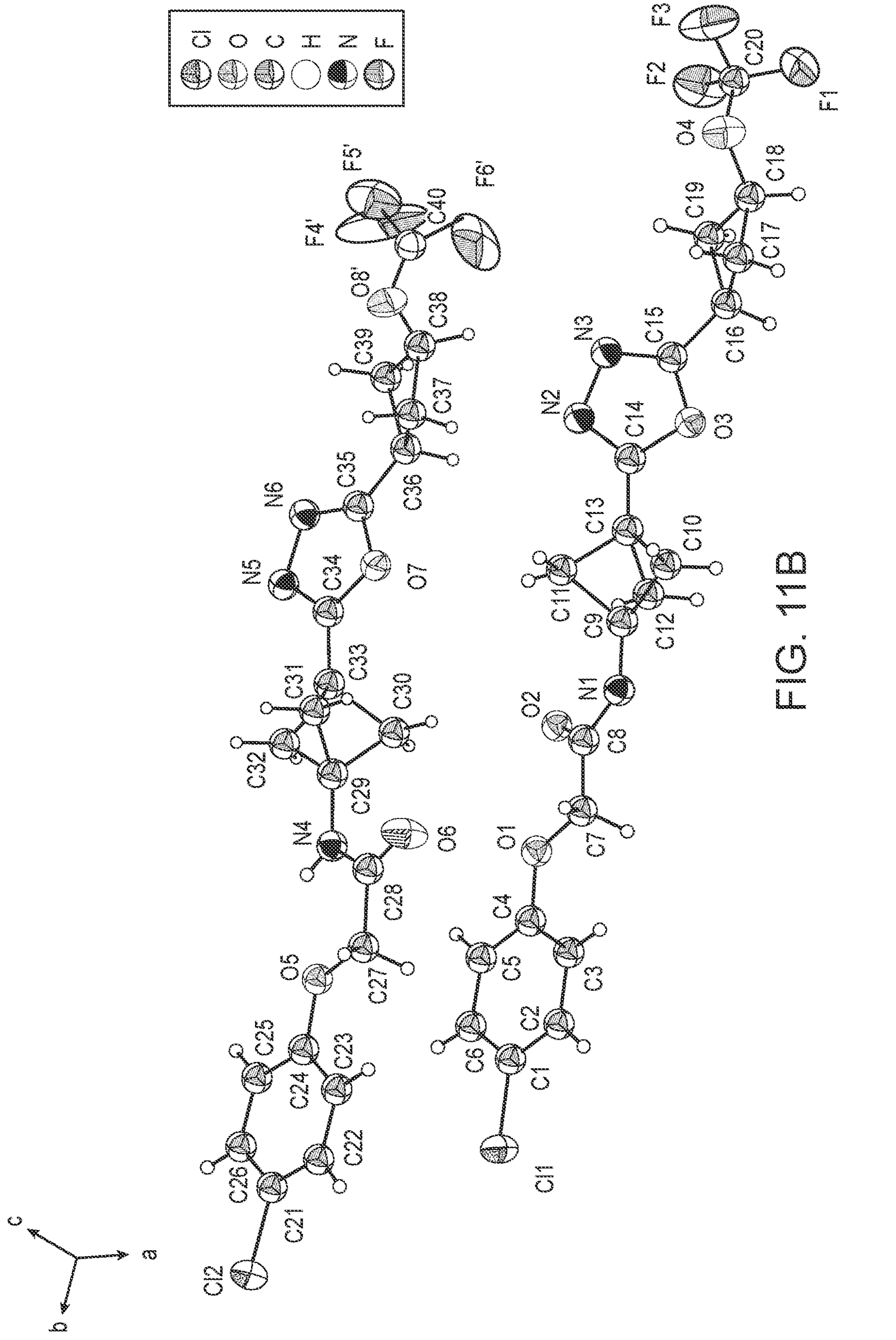
FIG. 11B shows thermal ellipsoid drawing of Compound I Form C asymmetric unit (Part 2 of the disorder in $—OCF_3$).

Form D was characterized by XRPD and DSC. The XRPD trace (FIG. 9) revealed a characteristic amorphous halo with no significant diffraction peaks. DSC from a heat-cool-heat DSC cycle showed the glass transition temperature of Form D to be around 27° C. (FIG. 8). These data show that Form D is amorphous and non-crystalline

Example 6. Interconversion Among Forms of Compound I

Forms A and C are stable anhydrous, crystalline forms, whereas Forms B and D are metastable forms.

Form B can only be prepared in a location where Form C has rigorously been excluded, otherwise the conditions to prepare Form B (described above) will instead produce Form C, the most thermodynamically stable form identified. When Form C has been excluded, Form B desolvates to Form A upon vacuum drying.

Form D will convert to Form C upon standing at room temperature or higher than room temperature (e.g., 25° C.-50° C.) for several days.

Form A slurry converts to Form C in the presence of Form C seed. For example, Form A (10 mg) and Form C (10 mg) were stirred in saturated IPA/water and MeCN/water at temperatures ranging from 5-60° C. After 6-8 days, the solids were analyzed by XRPD and DSC, and the results show that only Form C was present. These results indicate that Form C is thermodynamically more stable than Form A at temperatures of 5-60° C. The reverse experiment was also performed and showed that Form C is the more stable form—i.e., Form A could not be obtained by seeding Compound I solutions with Form A in locations where Form C had been prepared. Form A could only be prepared in a location uncontaminated with Form C (e.g., locations where From C had not previously existed).

TABLE 3

Slurry conditions for preparation of Form C from Form A

| Solvent system | Temperature (° C.) | Slurry Time (day) | Results |
|---|---|---|---|
| IPA/water (1:1) | 22 | 8 | Form C |
| ACN/water (1:2) | 22 | 8 | Form C |
| IPA/water (1:1) | 60 | 6 | Form C |
| ACN/water (1:2) | 60 | 6 | Form C |
| IPA/water (1:1) | 5 | 8 | Form C |
| ACN/water (1:2) | 5 | 8 | Form C |

Form A can be converted to Form C without seeding such as in a laboratory where Form C was previously produced. For example, Form A (3 g) was suspended in 1:1 IPA: heptane (24 mL) and heated to 60-65° C. to achieve complete dissolution. The solution was cooled to about 55° C., and heptane (24 mL) was added slowly. The resulting slurry was cooled to 0-5° C. and isolated by filtration. The resulting solids were found to be Form C by DSC analysis. When the above solution is seeded with Form A (0.1%), Form C crystals are still obtained. Table 4 below provides a summary of Compound I forms described herein.

TABLE 4

| Summary of Compound I Forms | | | | | |
|---|---|---|---|---|---|
| Form | TGA (wt loss %) | DSC (onset) | Crystalline Form | Hygroscopicity | Enthalpy (J/g) |
| Form A | 0.08% (to 150° C.) | 126.5° C. | Anhydrate | Non-hygroscopic | 72.5 |
| Form B | NA | NA | Metastable solvate | NA | NA |
| Form C | 0.25% (to 150° C.) | 132.3° C. | Anhydrate | Non-hygroscopic | 79.4 |
| Form D | NA | 26.8° C. ($T_g$) | Metastable amorphous | NA | NA |

Example 7. Biorelevant Media Solubility of Forms A and C

Biorelevant media solubility of Forms A and C were studied in water, SGF, FaSSIF, and FeSSIF at 37° C. 10-20 mg of Form A or C was weighed into 2-3 mL glass vials and media was added to achieve a solids loading of ~5 mg/mL. Each slurry was magnetically agitated at 750-1000 rpm at 37° C., filtered via centrifugation, and the supernatant was analyzed by HPLC to determine solubility. In all cases, there was no polymorphic form change observed by XRPD analysis of the filtered solids. The results are summarized in Table 5 below. Form C solubility was lower than Form A. Form C also has a higher melt temperature indicating that Form C is thermodynamically favored over Form A.

TABLE 5

| Solubility in Biorelevant Media | | | |
|---|---|---|---|
| Form | Media | Solubility (μg/mL) | Final XRPD |
| Form A | Water | 9.7 | Form A |
| | SGF | 46 | Form A |
| | FaSSIF | 25 | Form A |
| | FeSSIF | 44 | Form A |
| Form C | Water | 1.02 | Form C |
| | SGF | 0.56 | Form C |
| | FaSSIF | 9.65 | Form C |
| | FeSSIF | 16.14 | Form C |

Example 8. Stability of Forms A and C

To evaluate the solid form stability, Forms A and C were stored under 25° C./60% RH (open), 40° C./75% RH (open), and 60° C. for up to 4 weeks. Samples were analyzed by XRPD, TGA, DSC, and HPLC purity. No form change, weight gain, or purity changes were observed for either Forms A or C solids as shown in Table 6 below.

TABLE 6

| Stability of Form A and Form C | | | | | | |
|---|---|---|---|---|---|---|
| Form | Condition | Time point | XRPD | TGA loss (%, to 150° C.) | DSC endotherm (° C.) | HPLC purity % |
| Form A | — | Initial | Form A | 0.4 | 125.0 | 98.5 |
| | 25° C./60% | 1 week | Form A | 1.8 | 125.6 | 99.3 |
| | RH (open) | 4 week | Form A | 0.6 | 125.3 | 98.8 |
| | 40° C./75% | 1 week | Form A | 0.9 | 125.4 | 99.3 |
| | RH (open | 4 week | Form A | 0.7 | 125.1 | 98.7 |

TABLE 6-continued

| Stability of Form A and Form C | | | | | | |
|---|---|---|---|---|---|---|
| Form | Condition | Time point | XRPD | TGA loss (%, to 150° C.) | DSC endotherm (° C.) | HPLC purity % |
| | 60° C. | 1 week | Form A | 0.7 | 125.2 | 99.3 |
| | (open) | 4 week | Form A | 0.6 | 125.1 | 98.8 |
| Form C | — | Initial | Form C | 0.1 | 133.1 | 99.8 |
| | 25° C./60% | 2 week | Form C | 0.4 | 133.7 | 99.7 |
| | RH (open) | 4 week | Form C | 0.3 | 133.3 | 99.7 |
| | 40° C./75% | 2 week | Form C | 0.2 | 133.6 | 99.7 |
| | RH (open | 4 week | Form C | 0.2 | 133.3 | 99.8 |
| | 60° C. | 2 week | Form C | 0.3 | 133.6 | 99.8 |
| | (closed) | 4 week | Form C | 0.2 | 133.0 | 99.8 |

Example 9. Plasma Pharmacokinetic (PK) Study of Form A (Micronized and Unmicronized) Compared to Form C (Micronized) in Monkeys Non-naïve male cynomolgus monkeys were used in this study with at least a 7-day washout period prior to dosing Animals were administered micronized Form A, unmicronized Form A, or micronized Form C powder in capsule by single oral administration at 15 mg/kg. The capsules were prepared according to the animals' body weights on dosing day. Blood samples were collected at 0.25, 0.5, 1, 2, 4, 8, 24, 48, and 72 hours post-dose. Concentrations of Compound I in plasma samples were determined by LC/MS/MS and the data is provided in the table below.

| Polymorph | Particle size (d90) | Dose (mg/kg) | $AUC_{0-24\ h}$ (μM-hr) | $C_{max}$ (μM) | $T_{max}$ (hr) |
|---|---|---|---|---|---|
| Form A | 5 (micronized) | 15 | 154 ± 44 | 9.8 ± 4.1 | 8 |
| Form A | 43 (unmicronized) | 15 | 92 ± 24 | 5.6 ± 0.4 | 4 |
| Form C | 5 (micronized) | 15 | 117 ± 39 | 7.6 ± 3.4 | 4 |

Micronized Form A and Form C provided comparable exposure and PK profiles in cynomolgus monkeys dosed at 15 mg/kg. Unmicronized Form A showed relatively lower AUC and $C_{max}$ compared to micronized Form A.

Example 10. Plasma Pharmacokinetic (PK) Study of Form A and Form C in Rats

Wistar Han rats were administered a nanosuspension of Form A or Form C as a single oral administration at 25 mg/kg. The nanosuspensions were prepared by suspending nano-milled Form A or Form C in deionized water (2.5 mg/mL) to obtain opaque homogenous suspensions. Blood samples were collected at 0.25, 0.5, 1, 2, 4, 8, 24, 48, and 72 hours post-dose. Concentrations of Compound I in plasma samples were determined by LC/MS/MS.

| Form | Dose (mg/kg) | $AUC_{0-48\ h}$ (μM-hr) | $C_{max}$ (μM) | $T_{max}$ (hr) |
|---|---|---|---|---|
| Form A | 25 | 1700 ± 271 | 105 ± 8 | 8 |
| Form C | 25 | 1658 ± 211 | 101 ± 10 | 8 |

As thermodynamic stability and reduced solubility can lead to reduced bioavailability, it was surprisingly found that Form C is superior to Form A by having better stability while also having comparable systemic exposure (AUC and $C_{max}$).

Example 11. Plasma Pharmacokinetic (PK) Study of Form A and Form C in Monkeys

Non-naïve male cynomolgus monkeys were used in this study with at least a 7-day washout period prior to dosing Animals were administered a nanosuspension of Form C as a single oral administration at 25 mg/kg. The nanosuspension was prepared by suspending nano-milled Form C in deionized water (5 mg/mL) to obtain an opaque homogenous suspension. Blood samples were collected at 0.25, 0.5, 1, 2, 4, 8, 24, 48, and 72 hours post-dose. Concentrations of Compound I in plasma samples were determined by LC/MS/MS.

A separate study was performed for a nanosuspension of Form A.

Results of the Form C and Form A monkey studies are provided in the table below.

| Form | Dose (mg/kg) | $AUC_{0-24\ h}$ (μM-hr) | $C_{max}$ (μM) | $T_{max}$ (hr) |
|---|---|---|---|---|
| Form A | 25 | 451 ± 84 | 25.4 ± 4.1 | 4 |
| Form C | 25 | 367 ± 99 | 21.7 ± 4.2 | 8 |

As thermodynamic stability and reduced solubility can lead to reduced bioavailability, it was surprisingly found that Form C is superior to Form A by having better stability while also having comparable systemic exposure (AUC and $C_{max}$).

All patents and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of embodiments are exemplary and are not intended as limitations on the scope of the disclosure. Changes therein and other uses will occur to those skilled in the art, which are encompassed within the spirit of the disclosure, are defined by the scope of the claims.

The invention claimed is:

1. Form C polymorph of 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide, that exhibits an X-ray powder diffraction pattern having peaks expressed in ±0.2 degrees 2-theta at 18.5, 23.3, 25.1, and 25.8, wherein the X-ray powder diffraction pattern is made using CuKα radiation.

2. The Form C polymorph of claim 1, wherein the diffractogram further comprises one or more peaks expressed in ±0.2 degrees 2-theta selected from 17.3, 17.9, and 20.2.

3. The Form C polymorph of claim 1, wherein the diffraction pattern is substantially as shown in FIG. 5.

4. The Form C polymorph of claim 1, characterized by a differential scanning calorimetry (DSC) curve that shows an endotherm onset at about 132.3° C.

5. The Form C polymorph of claim 1, wherein the differential scanning calorimetry (DSC) curve is substantially as shown in FIG. 6.

6. The Form C polymorph of claim 1, wherein the dynamic vapor sorption (DVS) isotherm is substantially as shown in FIG. 7.

7. The Form C polymorph of claim 1, produced by subjecting a Form A polymorph of 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide that exhibits an X-ray powder diffraction pattern having peaks expressed in ±0.2 degrees 2-theta at 22.2, 22.6, and 22.9, wherein the X-ray powder diffraction pattern is made using CuKα radiation, to high energy milling.

8. Form A polymorph of 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide that exhibits an X-ray powder diffraction pattern having peaks expressed in ±0.2 degrees 2-theta at 22.2, 22.6, and 22.9, wherein the X-ray powder diffraction pattern is made using CuKα radiation wherein the compound is micronized.

9. The Form A polymorph of claim 8, wherein the diffractogram further comprises one or more peaks expressed in ±0.2 degrees 2-theta selected from 17.8, 20.0, 20.8, and 21.0.

10. The Form A polymorph of claim 8, wherein the diffraction pattern is substantially as shown in FIG. 1.

11. The Form A polymorph of claim 8, characterized by a differential scanning calorimetry (DSC) curve that shows an endotherm onset at about 126.5° C.

Figure 2:
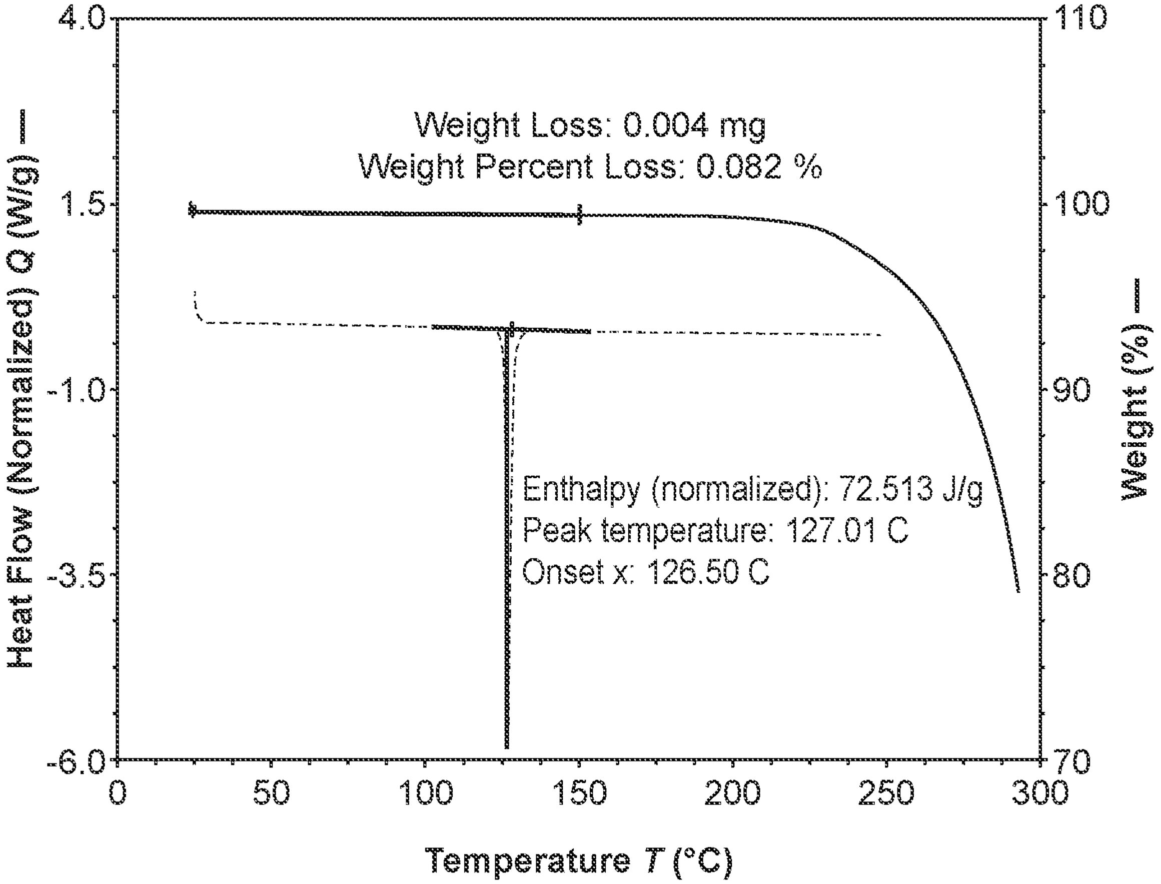
FIG. 2 is a thermogravimetric analysis (TGA) (top line) and a differential scanning calorimeter (DSC) curve (bottom line) of Compound I Form A.

12. The Form A polymorph of claim 8, wherein the DSC curve is substantially as shown in FIG. 2.

13. The Form A polymorph of claim 8, wherein the dynamic vapor sorption (DVS) isotherm is substantially as shown in FIG. 3.

14. The Form A polymorph of claim 8, produced by diffusion of vapor of a counter solvent onto a solution of 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide at room temperature.

15. A pharmaceutical composition comprising the polymorph of claim 1, and one or more pharmaceutically acceptable carriers.

16. The pharmaceutical composition of claim 15, wherein at least 95% of the 2-(4-chlorophenoxy)-N-[3-[5-[cis-3-(trifluoromethoxy)cyclobutyl]-1,3,4-oxadiazol-2-yl]-1-bicyclo[1.1.1]pent-1-yl]acetamide is in a crystalline form.

17. A method for treating a disease or condition mediated, at least in part, by eukaryotic initiation factor 2B, the method comprising administering to a patient in need thereof an effective amount of the Form C polymorph of claim 1.

18. The method of claim 17, wherein the disease or condition is a neurodegenerative disease.

19. The method of claim 17, wherein the disease is Alexander's disease, Alper's disease, Alzheimer's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, frontotemporal dementia, vanishing white matter disease, Gerstmann-Straussler-Scheinker syndrome, Huntington's disease, HIV-associated dementia, Kennedy's disease, Krabbe's disease, kuru, Lewy body dementia, Machado-Joseph disease (Spinocerebellar ataxia type 3), Multiple sclerosis, Multiple System Atrophy, Narcolepsy, Neuroborreliosis, Parkinson's disease, Pelizaeus-Merzbacher Disease, Pick's disease, Primary lateral sclerosis, Prion diseases, Refsum's disease, Sandhoffs disease, Schilder's disease, Subacute combined degeneration of spinal cord secondary to Pernicious Anaemia, Schizophrenia, Spinocerebellar ataxia (multiple types with varying characteristics), Spinal muscular atrophy, Steele-Richardson-Olszewski disease, insulin resistance or *Tabes dorsalis*.

20. The method of claim 17, wherein the disease is Alzheimer's disease, ALS, Parkinson's disease, or dementia.

21. The method of claim 20, wherein the dementia is frontotemporal dementia (FTD).

22. The method of claim 20, wherein the disease is ALS.

23. A method for treating a disease or condition mediated, at least in part, by eukaryotic initiation factor 2B, the method comprising administering to a patient in need thereof an effective amount of the Form A polymorph of claim 8.

* * * * *